United States Patent [19]

O'Sullivan et al.

[11] Patent Number: 5,270,334

[45] Date of Patent: Dec. 14, 1993

[54] 4-METHOXY-5-METHYL-PYRAN-3-OL NATURAL PRODUCTS AND DERIVATIVES THEREOF

[75] Inventors: Joseph O'Sullivan, Belle Mead, N.J.; Douglas W. Phillipson, New Haven, Conn.; Henner Straub, Regensburg; Peter H. Ermann, Donaustauf, both of Fed. Rep. of Germany

[73] Assignee: E. R. Squibb & Sons, Inc., Princeton, N.J.

[21] Appl. No.: 908,767

[22] Filed: Jul. 1, 1992

Related U.S. Application Data

[63] Continuation of Ser. No. 723,292, Jun. 28, 1991, abandoned, which is a continuation-in-part of Ser. No. 305,338, Jan. 31, 1989.

[51] Int. Cl.⁵ .................... A01N 43/16; C07D 309/10
[52] U.S. Cl. ..................................... 514/459; 549/417
[58] Field of Search ............... 549/417, 415; 514/460, 514/459, 422, 336, 231.5, 252; 548/517; 546/207; 544/336, 149

[56] References Cited

U.S. PATENT DOCUMENTS 4,952,604  8/1990  Hensens et al. ................. 514/459

FOREIGN PATENT DOCUMENTS 56-18592  2/1981  Japan .

OTHER PUBLICATIONS

*Journal of Medicinal Chemistry*, vol. 32, No. 10 (Oct. 1989) pp. 2231–2239.
Schwartz et al., *Journal of Antibiotics*, vol. 44, No. 5 (May 1991), pp. 463–471.

*Primary Examiner*—Nicky Chan
*Attorney, Agent, or Firm*—Theodore R. Furman, Jr.; Ellen K. Park

[57] ABSTRACT

Novel antibiotic substances, including novel natural products, having the general formula

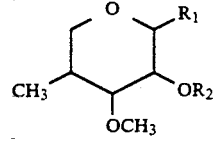

wherein $R_1$ and $R_2$ are as defined herein, are disclosed. These compounds have been found to be cytochrome P450 inhibitors.

6 Claims, 8 Drawing Sheets

4-METHOXY-5-METHYL-PYRAN-3-OL NATURAL PRODUCTS AND DERIVATIVES THEREOF

This is a continuation of copending applications Ser. No. 723,292 filed on Jun. 28, 1991, now abandoned, which is a continuation-in-part of Ser. No. 305,338 filed on Jan. 31, 1989 pending.

SUMMARY OF THE INVENTION

In accordance with the present invention, novel compounds having antibiotic and cytochrome P450 inhibition activity are disclosed. These compounds have the general formula

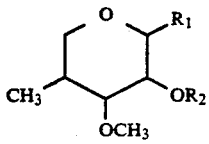

wherein
$R_1$ is alkyl, alkenyl, arylalkyl, arylalkenyl,

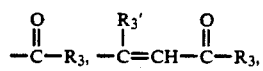

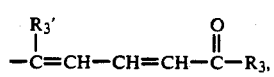

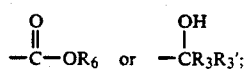

$R_2$ is hydrogen, a duitable protecting group such as

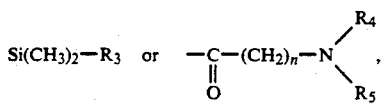

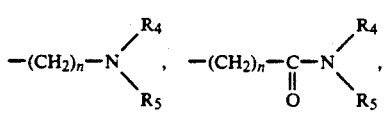

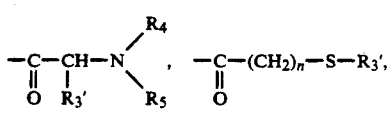

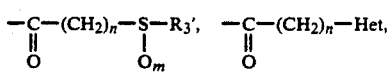

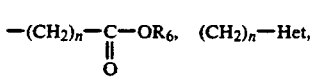

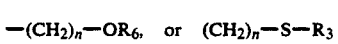

(wherein Het is heteroaryl such as imidazolyl, oxazolyl, thiazolyl, triazolyl, pyridyl or pyrimidinyl);
$R_3$ and $R_3'$ are independently hydrogen, alkyl or arylalkyl;
$R_4$ and $R_5$ are independently selected from hydrogen, alkyl, arylalkyl, aryl or

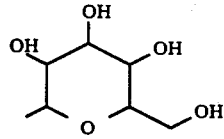

or $R_4$ and $R_5$ taken together with the nitrogen atom to which they are attached complete a heterocyclic ring selected from pyrrolidinyl, piperidyl, pyrazinyl or morpholinyl;
$R_6$ is hydrogen or a suitable protecting group;
$m = 1$ to 2; and
$n = 1$ to 4.

Also within the scope of this invention are natural products, methods for their preparation and methods for their use. The natural products are useful, for example, as antifungal agents, as cytochrome P450 enzyme inhibitors and in the synthesis of other derivatives of formula I, and have been found to have the structures

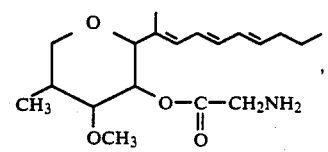

having the trivial name scopularin,

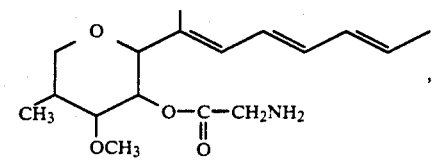

having the trivial name lanomycin,

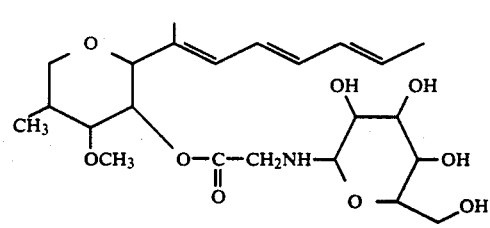

and the alcohol derivative

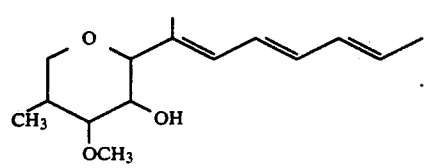

DETAILED DESCRIPTION OF THE INVENTION

Figure 1:
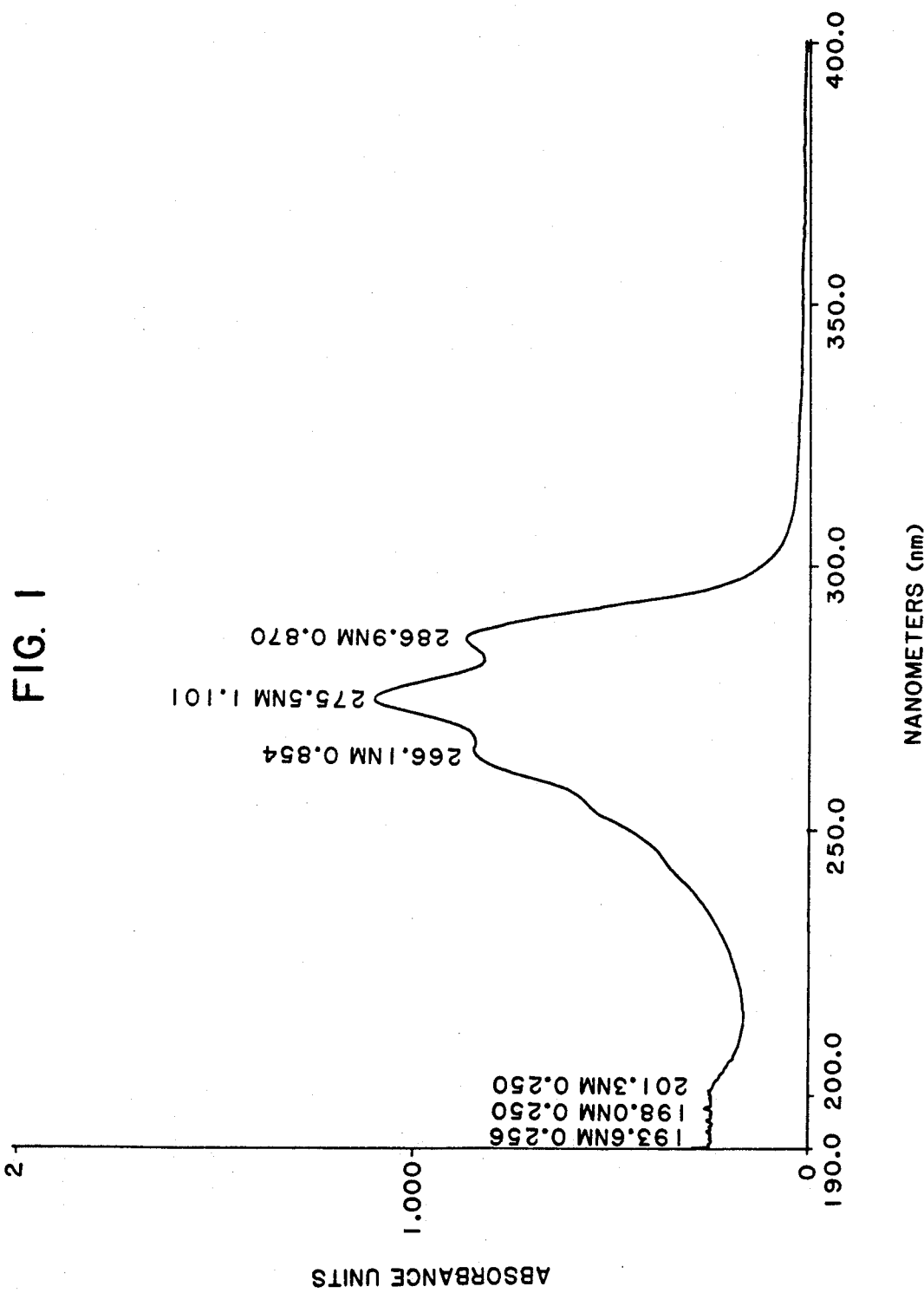
FIG. 1 is the ultraviolet spectrum of scopularin recorded in methanol.

The following definitions apply to the corresponding terms as they are used throughout this application.

The term "alkyl", as used throughout the specification either by itself or as part of a larger group, refers to groups having 1 to 12 carbon atoms. Alkyl groups having 1 to 4 carbon atoms are preferred, except in the case of $R_1$ where groups having 8 to 10 carbon atoms are preferred.

The term "alkenyl", as used throughout the specification either by itself or as part of a larger group, refers to both straight and branched chain groups. Those groups having 2 to 12 carbon atoms are preferred and groups having 5-10 carbons are most preferred.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

Cultivation of a strain of the microorganism Scopulariopsis sp. which has been deposited in the American Type Culture Collection as A.T.C.C. No. 20,914 yields a novel antibiotic substance of formula Ia, hereinafter referred to by the trivial chemical name "scopularin". The antibiotic has activity against a variety of yeasts and fungi, and has also been found to inhibit cytochrome P450 enzymes, such as lanosterol demethylase. The alcohol derivative of scopularin is also an inhibitor of cytochrome P450 enzymes, such as lanosterol demethylase.

Cultivation of a strain of the microorganism *Pycnidiophora dispersa*, which has been deposited in the American Type Culture Collection as A.T.C.C. No. 74,021, yields the antibiotic substance of formula Ib, hereinafter referred to by the trivial chemical name "lanomycin" and also the novel substances of formula Ic and IIb. Lanomycin, compound Ic has activity against a variety of yeasts and fungi and lanomycin and compound Ic have also been found to inhibit cytochrome P450 enzymes, such as lanosterol demethylase.

In addition to being useful as pharmaceutical agents, the natural products shown above are useful for the preparation of the synthetic compounds of formula I and the preparation of such compounds will now be described.

To prepare the compounds of formula I where $R_2$ is

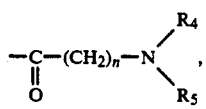

an alcohol of the formula

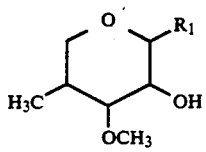

II is reacted with a compound of the formula

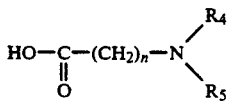

III (or an N-protected form thereof when one of $R_4$ or $R_5$ is to be hydrogen) in the presence of a coupling agent, e.g., dicyclohexylcarbodiimide, and in a solvent such as dichloromethane to provide the products

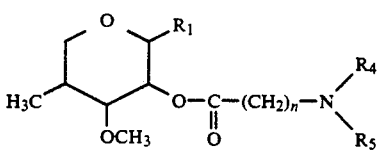

IV (which is protected when $R_4$ or $R_5$ is a protecting group).

To provide compounds of formula I wherein $R_2$ is

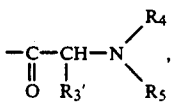

a compound of the formula

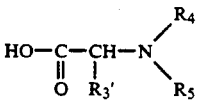

V is reacted with a compound of formula II to provide a compound of the formula

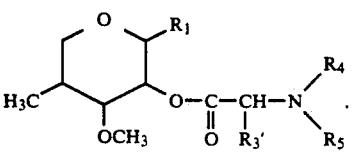

VI

To provide compounds of formula I where $R_2$ is

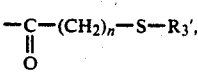

a compound of the formula

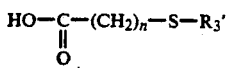 VII (or an S-protected form thereof when $R_3'$ is to be hydrogen) is reacted with an alcohol of formula II to provide

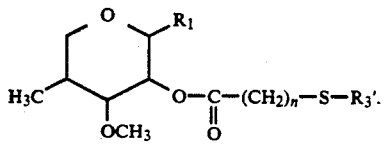 VIII

To provide compounds of formula I where $R_2$ is

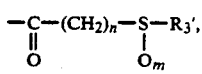

a compound of the formula

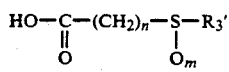 IX is reacted with an alcohol of formula II to provide

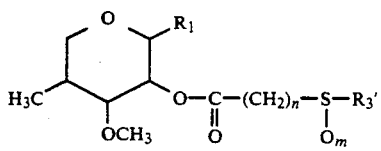 X in the presence of a coupling agent, e.g., ethyl-3-(3-dimethylamino)propyl carbodiimide and an acylation catalyst, e.g., 4-dimethylaminopyridine, and in a solvent such as dichloromethane. The sulfoxides of formula IX, $m=1$ and the sulfones of formula IX, $m=2$ are accessed by oxidation of compounds of formula VII by means of hydrogen peroxide in a solvent such as acetone or acetic acid.

To provide compounds of formula I wherein $R_2$ is

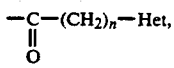

a compound of the formula

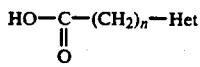 XI is reacted with the formula II to provide a compound of the formula

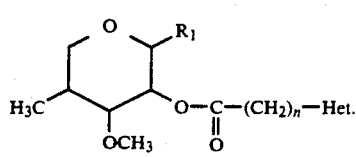 XII

Alternatively, compounds of formula XII wherein the heterocyclic group (Het) is attached to the alkyl chain —$(CH_2)_n$— via an N-atom can be prepared by first reacting an alcohol of formula II with a compound of the formula

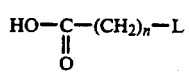 XIII (wherein L is a leaving group such as halogen)
in a solvent, e.g., tetrahydrofuran, and in the presence of a coupling agent, e.g., dicyclohexyl-carbodiimide, to provide a compound of the formula

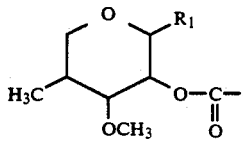 XIV

This intermediate XIV can thereafter be reacted with the desired heterocyclic compound, e.g., imidazole in the presence of a catalyst, e.g., sodium iodide, to provide the corresponding compound of formula XII.

To provide compounds of formula I wherein $R_2$ is —$(CH_2)_n$—COO—$R_6$, an alcohol of formula II is alkylated with a compound of the formula $$L-(CH_2)_n-COO-R_6 \quad XV$$

wherein $R_6$ is alkyl, arylalkyl or another suitable protecting group and L is a leaving group such as diazo or halogen to provide a compound of the formula

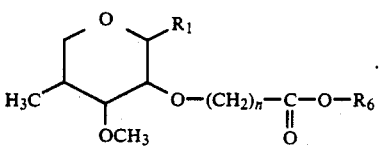 XVI

Diazo compounds of formula XV, wherein L is nitrogen, in the presence of a catalyst such as rhodium acetate are preferred when the substituent $R_1$ of the alcohol of formula II is alkyl or arylalkyl. Halo compounds of formula XV, wherein L is Cl, Br or J, are preferred when the substituent $R_1$ of the alcohol of formula II is alkenyl. In this case the alcohol of formula II is first treated with a base such as sodium hydride or thallium ethoxide to form the corresponding salt and then with the halo compound of formula XV.

To provide compounds of formula XVI, wherein $R_6$ is hydrogen, the esters of formula XVI, wherein $R_6$ is alkyl, arylalkyl or another suitable protecting group, were treated with a base, e.g., potassium hydroxide, in a solvent, e.g., methanol or were deprotected by another usual method.

To prepare compounds of formula I, wherein

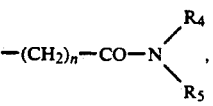

compounds of formula XVI wherein R$_6$ is alkyl, arylalkyl can be treated with ammonium hydroxide or an amine

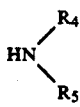

in the presence of a solvent such as isopropanol, to provide compounds of the formula

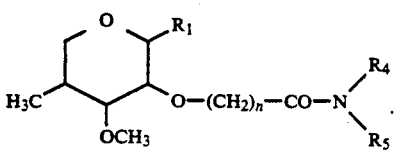
XVII

Alternatively, a compound of formula XVI, wherein R$_6$ is hydrogen can be reacted with an amine

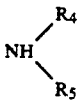

in the presence of a coupling agent such as dicyclohexylcarbodiimide.

To prepare compounds of formula I wherein R$_2$ is —(CH$_2$)$_n$—OH, a compound of formula XVI, wherein R$_6$ is alkyl or arylalkyl can be reduced with complex hydrides such as lithium aluminum hydride, in a solvent, e.g., tetrahydrofuran, with the proviso that the ester moiety attached to the 3-oxygen should be —(CH$_2$)$_{n-1}$—COO—R$_6$, to provide a compound of the formula

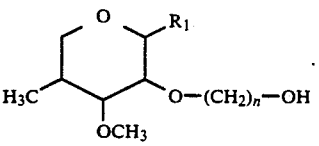
XVIII

Alcohols of formula XVIII can be converted to intermediates of the formula

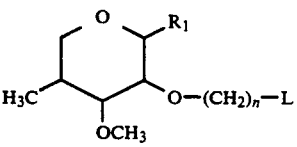
XIX wherein L is a leaving group, such as O-tosyl, N$_3$, NH$_2$, or another suitable group for a subsequent functional group interconversion, such as O-tosyl, SCOCH$_3$, SH.

To prepare compounds of formula I wherein R$_2$ is

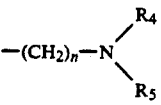

and R$_4$=R$_5$=hydrogen, compounds of the formula XVIII can be treated with a sulfo-chloride such as tosyl chloride, followed by a metal azide, e.g., NaN$_3$ in a solvent such as dimethylformamide, followed by lithium aluminum hydride in a solvent such as tetrahydrofuran to provide compounds of the formula

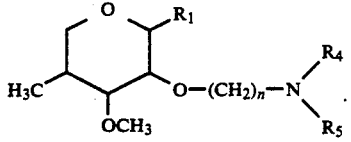
XX

Alternatively, to provide amines of formula XX, amides of formula XVII can be reduced with complex hydrides such as sodium borohydride in the presence of an acid, e.g., methanesulfonic acid, in a solvent, e.g., dimethylsulfoxide, with the proviso that the amide moiety attached to the 3-oxygen should be

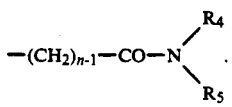

Compounds of formula I wherein R$_2$ is —(CH$_2$)$_n$—S—R$_3'$ can be prepared by functional group interconversion of alcohols of the formula XVIII via intermediates of the formula XIX to provide compounds of the formula

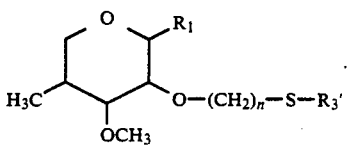
XXI

The alcohol of formula XVIII is reacted with a sulfochloride such as tosyl chloride, followed by a thiolate salt. Using potassium thiol acetate as thiolate salt, provides a compound of formula XXI, wherein R$_3'$ is acetyl and which can be treated thereafter with a base, e.g., potassium hydroxide, in a solvent, e.g., methanol, to provide a compound of formula XXI, wherein R$_3'$ is hydrogen.

To prepare compounds of formula I wherein R$_2$ is (CH$_2$)$_n$—Het, the heteroaryl-alkyl moiety can be introduced by alkylation of a salt of an alcohol of the formula II, e.g., sodium- or thallium salt, with a compound of the formula

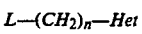
L—(CH$_2$)$_n$—Het        XXII (or N-protected form thereof when the heteroaryl ring has a NH ring atom, e.g., in imidazoles) to provide a compound of the formula

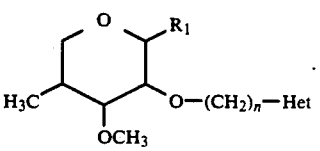
XXIII

Analogously, compounds of the formula I, wherein R$_2$ is —Si(CH$_3$)$_2$—R$_3$ or another suitable protecting group can be prepared by reacting an alcohol of formula II with corresponding reactive chlorides such as chloro-silanes, chloromethylethers or acid chlorides by standard methodology.

Compounds of formula I where R₁ is alkyl, alkenyl, arylalkyl or arylalkenyl can be prepared from compounds of formula IIa or IIb which are the alcohol derivatives of scopularin and lanomycin, respectively. These alcohols of formula IIa and IIb are easily obtained by treating the natural product scopularin of formula Ia and lanomycin of formula Ib respectively with a base, e.g., sodium bicarbonate, in a solvent, e.g., methanol. The alcohol of formula IIb can also be obtained as natural product using fermentation and isolation procedures which follow.

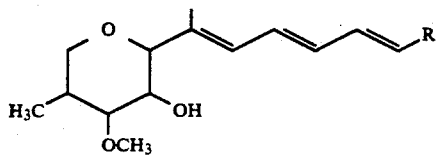

IIa alcohol of scopularin (R = CH₂—CH₂—CH₃)
IIb alcohol of lanomycin (R = CH₃)

Standard methodologies can be utilized to modify the R₁ side chain of alcohol IIa or IIb as desired. For example, reduction which may be accomplished by subjecting compound IIa or IIb to hydrogen gas in the presence of a palladium or carbon catalyst in a solvent, e.g., methanol, provides partially hydrogenated intermediates or the totally hydrogenated intermediates IIa' and IIb' respectively.

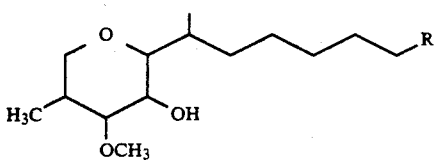

IIa' totally reduced alcohol of scopularin
(R = CH₂—CH₂—CH₃)
IIb' totally reduced alcohol of lanomycin
(R = CH₃)

These so-modified alcohols can thereafter be reacted as generally described above for alcohol II to provide the corresponding products of formula I.

Also standard methodologies can be utilized to degrade and modify the R side chain of alcohol IIa or IIb as described. For example, treatment of compound Ib, wherein R₂ is a protecting group such as Si(CH₂)₂—R₃,

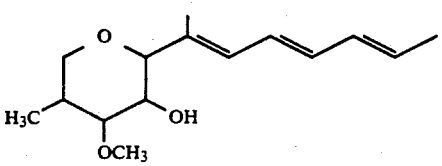

Ib with ozone at reduced temperatures in dichloromethane in the presence of pyridine provides products of formula I having the structures XXIV, XXV and XXVI.

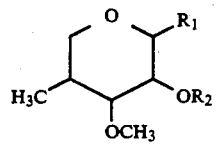

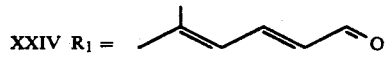

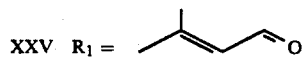

Further degradation of the R₁ side chain in compound XXVI can be accomplished for example by treatment of compound XXVI with a mixture of a steric hindered base, e.g., lithium diisopropylamide, and a silylating agent, e.g., t-butyldimethylsilylchloride, at reduced temperatures to provide the enolether of formula

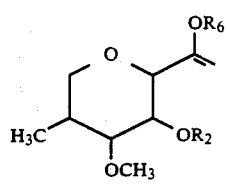

XXVII which in turn can be reacted with ozone in dichloromethane in the presence of pyridine at reduced temperatures to provide the ester of formula

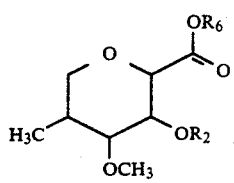

XXVIII or after reductive work-up by treatment of the so-formed ester XXVIII with lithium aluminium hydride in a solvent such as tetrahydrofuran to provide the alcohol

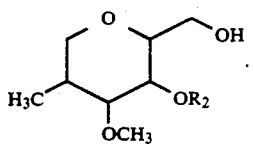

XXIX

To prepare a compound of formula I wherein R₁ is —CO—R₃ and R₃ is hydrogen and R₂ is a protecting group, e.g., Si(CH₂)₂—t.Bu, a compound of formula XXIX can be oxidized with oxalylchloride in the presence of dimethylsulfoxide and triethylamine at reduced temperatures to provide a compound of the formula

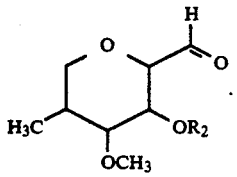

XXX

Starting from the compounds of formula XXIV to XXX other side chain derivatives of formula I, wherein $R_1$ is alkyl, arylalkyl, alkenyl or arylalkenyl can be prepared using standard methodology.

All stereochemical isomers (diastereomers and enantiomers) as well as all geometrical isomers (E,Z-isomers) of compounds of formula I are within the scope of the invention. Preferred compounds are those of structure

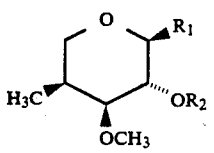

I' wherein $R_2$ is —CO—CH$_2$—NH$_2$ and $R_1$ is alkyl, alkenyl or arylalkenyl. Most preferred are those compounds of formula I where $R_2$ is selected from

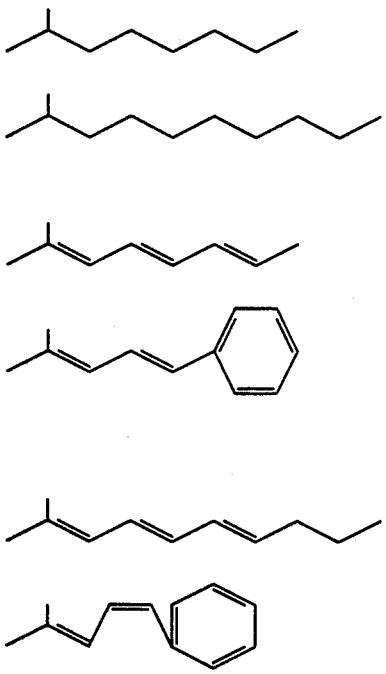

The Microorganism for Scopularin of Formula Ia

The microorganism used for the production of scopularin is a strain of Scopulariopsis isolated from a soil sample collected from St. Paul's Gate, Rome, Italy. A subculture of the organism can be obtained from the American Type Culture Collection, Rockeville, Maryland. Its accession number in this repository is A.T.C.C. No. 20,914. In addition to the specific microorganism described and characterized herein, it should be understood that mutants of the microorganism produced through the use of chemical or physical mutagens can also be cultivated to produce the subject compound.

The microorganism can be isolated from a soil sample in which it is present by placing 0.5 gram of the soil in 10ml of the following sterile buffer:

| | |
|---|---|
| NaCl | 8.5 g |
| KH$_2$PO$_4$ | 0.3 g |
| Na$_2$HPO$_4$ | 0.6 g |
| Gelatin | 0.1 g |
| Distilled Water to | 1000 ml |

The sample is mixed by vortexing and then sonicated for 10 minutes in an ultrasonic water bath. A series of dilutions are then prepared in the above buffer and 0.1 ml aliquots of the dilutions are spread-plated onto the following agar medium in order to obtain isolated colonies:

| | |
|---|---|
| Yeast extract | 2.0 g |
| Glucose | 5.0 g |
| Ocgall | 5.0 g |
| Sodium propionate | 1.0 g |
| CaCO$_3$ | 3.0 g |
| Agar | 2.0 g |
| V-8 Juice | 2 ml |
| Distilled Water | 800 ml |
| pH adjusted to 6.8 | |

The medium is autoclaved at 121° C. for 15 minutes. Chlorotetracycline (30 mg/liter) and streptomycin (30 mg/liter) are added to the medium before dispensing into petri dishes.

After 5 days incubation at 25° C., colonies of Scopulariopsis sp. A.T.C.C. No. 20,914 are isolated from the plated samples. The isolated colonies are then grown on potato dextrose agar.

Colonies of Scopulariopsis sp. on potato-dextrose agar (PDA) grow rapidly with the leading edge of growth submerged in the agar. Surface growth from the center out is zonate with alternating bands of pinkish-buff to avellaneous (grey tinged with pink) in color. The reverse is brownish-orange with the center a deep burgundy red. The surface texture is lanose (wooly) with sporulation covering the agar plate. A deep burgundy exudate is produced on the aerial mycelium which upon drying produces craters giving the mycelial mat a pock-marked appearance.

On cornmeal agar growth of Scopulariopsis sp. is thin transparent and pinkish-grey in color. The reverse color is a mouse grey. Surface texture is lanose with droplets of colorless exudate clinging to aerial hyphae. With age the exudate becomes a burgundy red color tingeing the underlying agar. Heavy sporulation gives the culture a salt and pepper appearance. There is no evidence of formation of coremia or perithecia.

Hyphae of Scopulariopsis sp. are hyaline (colorless) when young, irregularly becoming fuscous (brownish-grey) with age. They are 1.5-2 μm in diameter. Sporulation occurs from the terminus of annellophores which are flask-shaped structures tapering to a narrow opening. Annellophores may occur singly or in verticils of 3–4.5×2 μm in size.

The spores are produced within the annellophore by successive division of a mother nucleus and pass through this opening forming chains of varying length. Each successive spore formed leaves a characteristic scar on the outer wall of the annellophore. Spores are thick-walled with a truncate base occasionally with a small collarette attached. They are spherical to subovate, smooth and 3 μm in diameter. When first formed they appear smooth becoming rough with age. They have a longitudinal line which in fact is a thin-walled slit through which the germ tube passes at germination.

The following key diagnostic characters provide the basis for assigning the producing organism to the form-genus Scopulariopsis.

1. absence of coremia or perithecia;
2. annellidic sporulation;
3. presence of scars on the outer wall of the annellophore;
4. spore germination through a longitudinal germinal slit;
5. spores with truncate ends separated by a collarette;
6. spores borne in chains.

The Antibiotic Scopularin (Ia)

The antibiotic scopularin can be produced by cultivating Scopulariopsis sp. A.T.C.C. No. 20,914 at, or near, 25° C. under submerged aerobic conditions in an aqueous nutrient medium containing assimilable carbohydrate and nitrogen sources. The fermentation is carried out until substantial activity is imparted to the medium, usually about 72 to 76 hours.

After three days the broths are pooled and filtered. The cell mass is extracted with methanol and the concentrated methanol extract is chromatographed on silica gel eluting with a methanol-chloroform step gradient. Final purification of the active fraction from the silica gel column is achieved using an Ito counter current chromatography coil with a heptane-ethyl acetate-methanol-buffer system.

Alternatively, the whole broth may be extracted with ethyl acetate and the concentrated organic phase partitioned in ethyl acetate/methanol/water (5:2:5). The activity partitions into the lower phase while most of the mass remains in the upper phase After removal of the methanol vacuo from the lower phase, the activity is re-extracted into ethyl acetate. The concentrated ethyl acetate layer is purified using the Ito and silica gel steps mentioned above.

Figure 2:
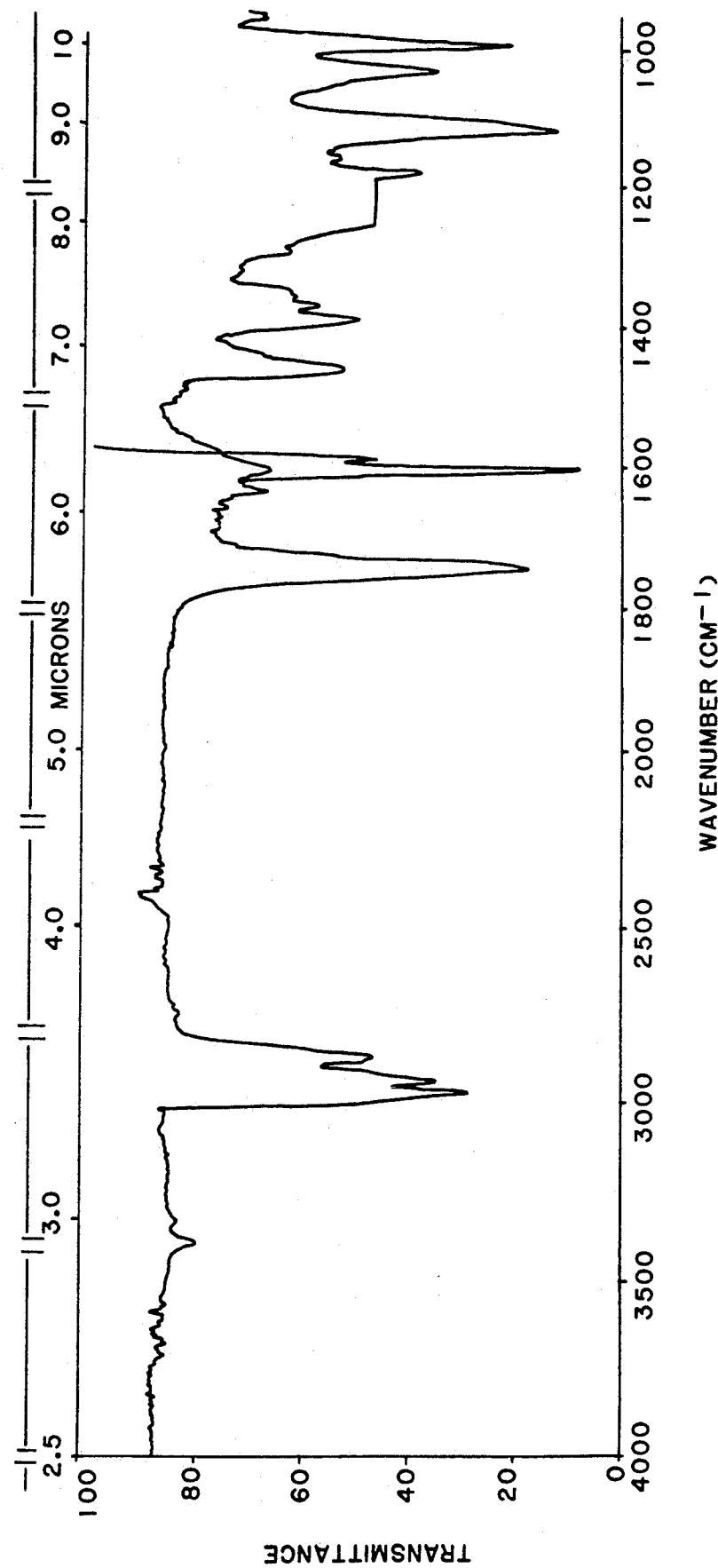
FIG. 2 is the infrared spectrum of scopularin recorded in chloroform.
Figure 3:
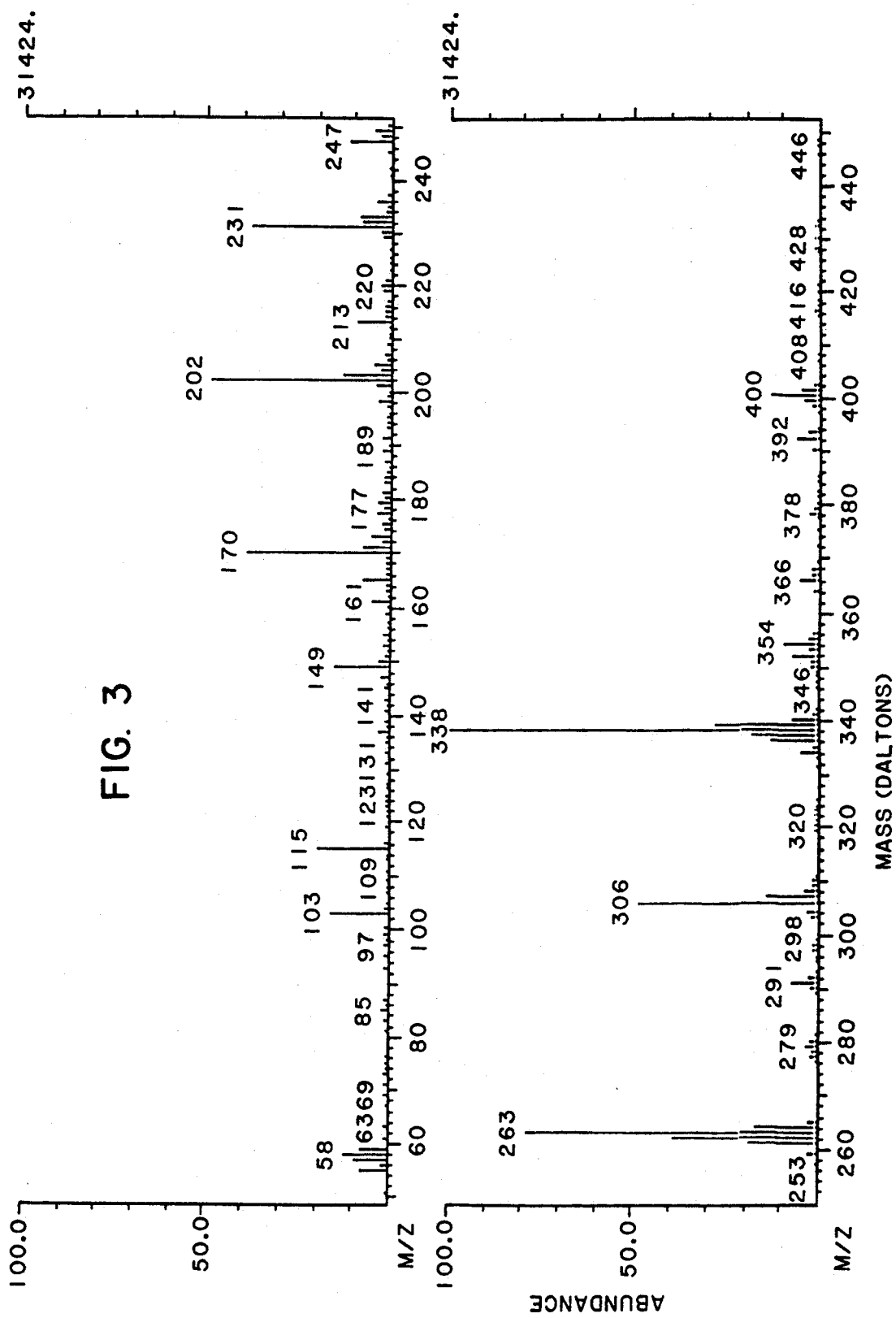
FIG. 3 is the positive ion chemical ionization mass spectrum of scopularin.
Figure 4:
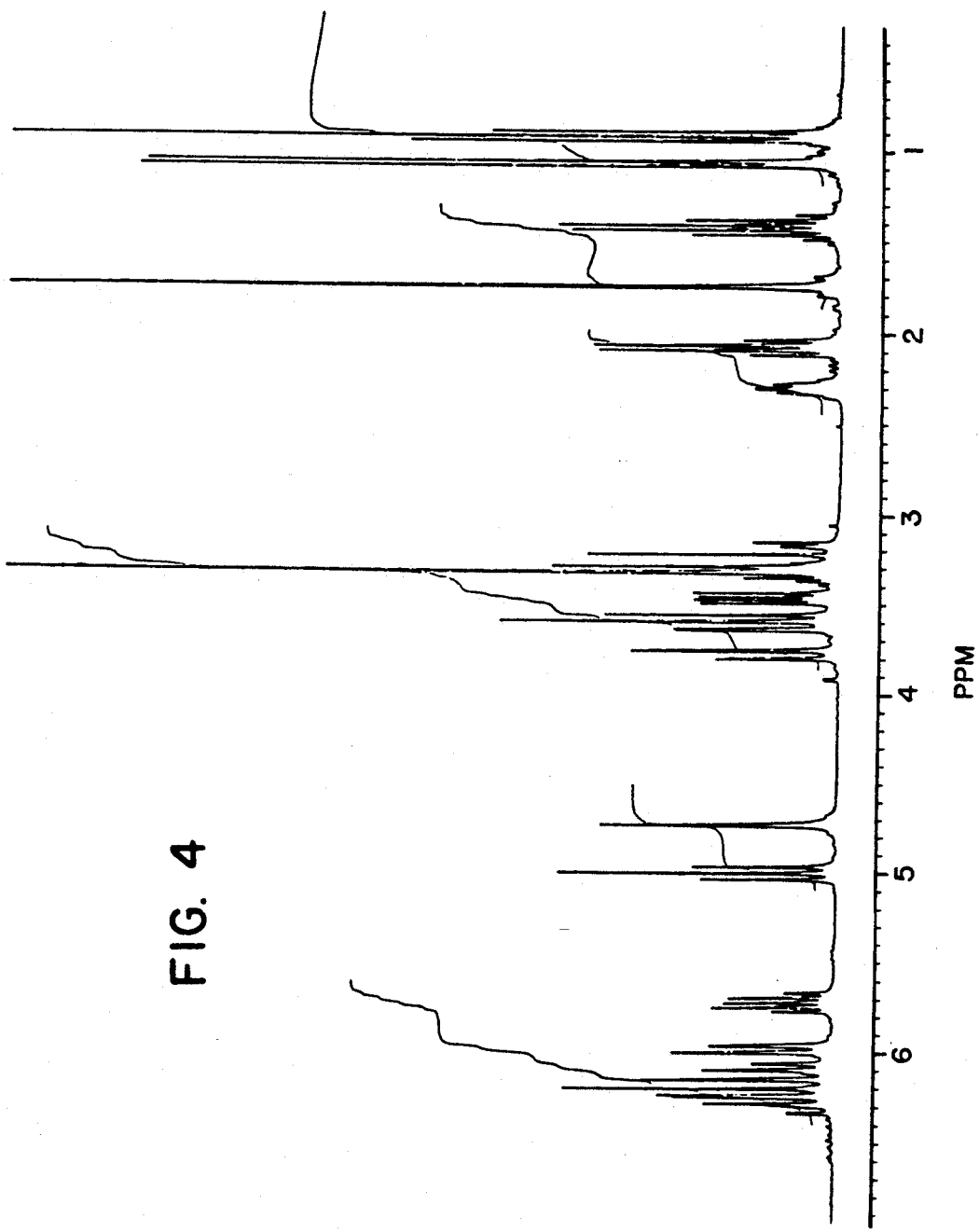
FIG. 4 is the 270 MHz $^1$H NMR spectrum of scopularin recorded in deuteromethanol.
Figure 5:
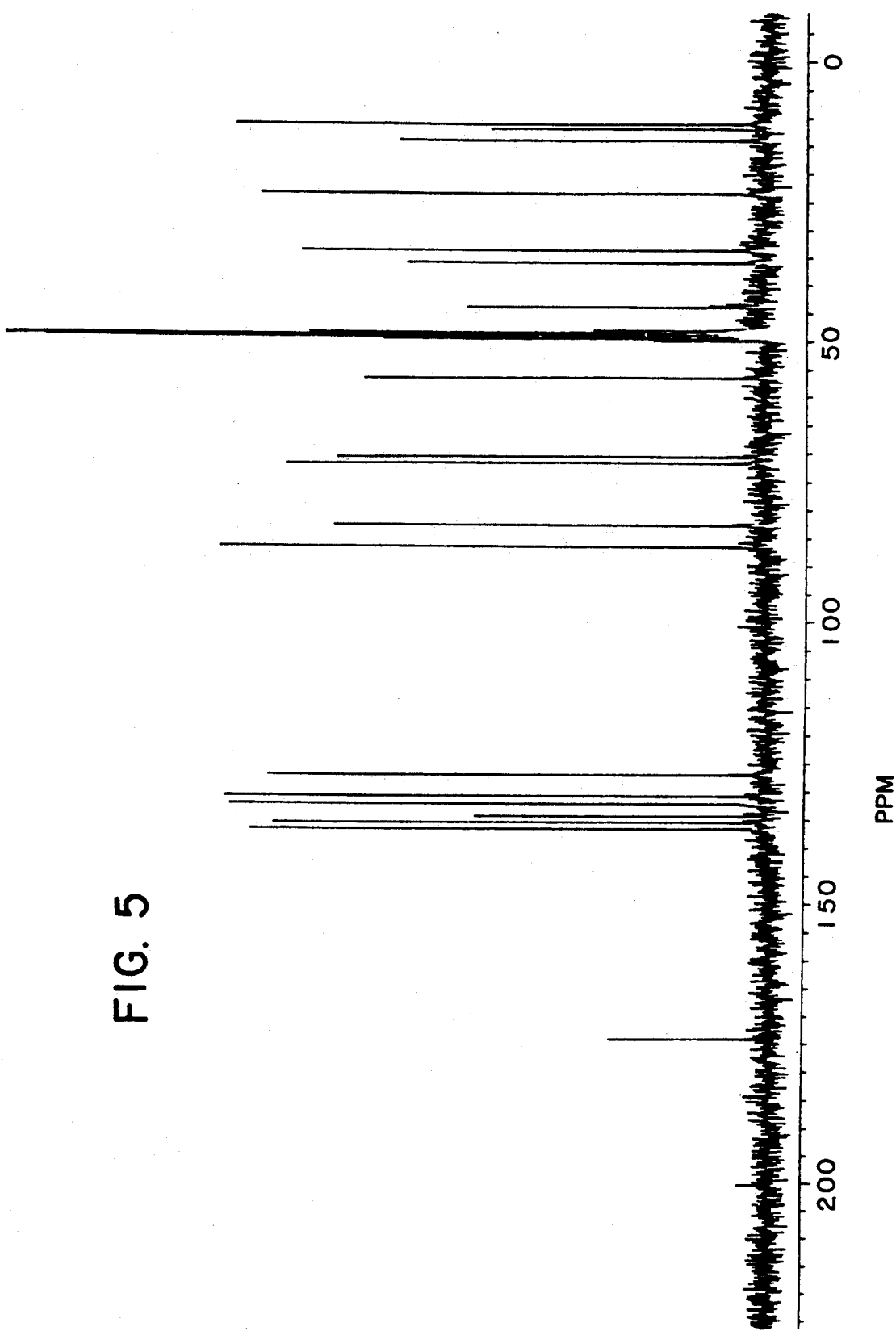
FIG. 5 is the 67.5 MHz $^{13}$C NMR spectrum of scopularin recorded in deuteromethanol.

The UV spectrum of scopularin, recorded in methanol, has an absorption maximum at 275 nm with an extinction coefficient of 37,000. Shoulders on the main band can be seen at 266 and 286 nm. The UV spectrum of scopularin is shown in FIG. 1. There were no observable changes in the spectrum when recorded in acid or base. The Infra-red spectrum recorded in chloroform is reproduced as FIG. 2. Prominent bands are observable at 2970, 2940, 2860, 1740, 1460, 1390, 1115, 1030 and 990 cm$^{-1}$. The positive ion chemical ionization mass spectrum is given in FIG. 3. In addition to the pseudo-molecular ion at 338 daltons, other fragment ions can be observed at m/z 306, 263, 231, 202 and 170. A high resolution mass measurement of the [M+H]$^+$ ion in the Fast Atom Bombardment mass spectrum yielded a value of 338.2310. The exact mass calculated for the formula $C_{19}H_{32}NO_4$ is 338.2331. The 270 MHz proton spectrum recorded in deuteromethanol is depicted in FIG. 4. The 67.5 MHz carbon spectrum (also recorded in deutero methanol solution) is given in FIG. 5. The resonances and multiplicities determined from INEPT spectra (not shown) are as follows: 174.12(s), 136.54(d), 135.42(d), 134.27(s), 132.08(d), 130.75(d), 127.01(d), 86.61(d), 82.78(d), 71.75(t), 70.71(d), 56.63(q), 43.90(t), 35.96(t), 33.71(d), 23.54(t), 13.98(q), 11.88(q), 11.08(q).

Scopularin has a TLC $R_f$ of 0.4 when chromatographed on E. Merck Kieselgel 60 $F_{254}$ 5×10 cm plates using a chloroform/methanol (19:1) solvent system. An HPLC system consisting of a Varian 5020 LC, Spectra-Physics 4290 integrator, Perkin-Elmer CR $C_{18}$ 3×3 column, 1 mL/min. flow rate, with acetonitrile as the organic modifier and a 0.1M ammonium acetate (adjusted to pH 4.5 with acetic acid) buffer system, UV detection at 260 nm, was used. With a gradient composed of the following program of linear segments; T=0, 30% Organic, T=5 min., 50%, T=9.5 min., 100%, hold at 100% till 12 min. then back to 30% at 13 min., re-equilibrate at 30% for 3.5 min. between injections, scopularin has a retention time of approximately 6.6 min.

The Microorganism for Lanomycin of formula Ib and for the Compounds of formula Ic and IIb The fungus is a strain of Pycnidiophora dispersa and was isolated from a soil sample collected in Culpepper, Virginia. A subculture of the organism can be obtained from the American Type Culture Collection, Rockeville, Maryland. Its accession number in this repository is A.T.C.C. No. 74,021. In addition to the specific microorganism described and characterized herein, it should be understood that mutants of the microorganism produced through the use of chemical or physical mutagens can also be cultivated to produce lanomycin and the alcohol thereof.

The microorganism can be isolated from a soil sample containing same by the procedures and media discussed above for Scopulariopsis.

Colonies of the fungus grew well on potato-dextrose agar and tomato juice agar. The sexual fruiting bodies (cleistothecia) were produced readily on these media but required 5 to 6 weeks for the ascospores borne within to mature. Cleistothecia were dark brown to black with an outer wall (peridium) composed of a single layer of polygonal pseudoparenchyma cells. Plates composed of radiating cells delineating lines of cleavage of the peridium were not evident. Cleistothecia occurred singly or in clusters but each had its own peridium.

Sac-like asci were produced from fertile hyphae randomly distributed within the lumen of the cleistothecium. Histological examination of thin sections of the ascus cell wall showed it to be unitunicate. Each ascus bore ascospores in multiples of eight depending on the stage of division. The ascospores were elliptical, pigmented and partially septate with an oil globule at each end. They were not bivalve and did not possess a longitudinal germinal slit. They germinated by means of a terminal or lateral germ tube. Ascospores were 4.7×2.5 u. Paraphyses, specialized filiform cells interspersed among the asci, were lacking.

The asexual cycle consisted of pycnidia which were ovoid bodies with an ostiole or pore. Conidia were borne on short conidiophores which lined the inner layer of the pycnidium. When the central cavity of the pycnidium was filled with spores, they were released through the ostiole in a slime. Conidia were elliptical, smooth, hyaline and averaged 3×2 u in size. Monoconidial isolates produced cultures which fruited both sexually and asexually, as, indeed, did monoascospore cultures. This agreed with the original observation by Clum (1955) which formed the basis for the identification of Pycnidiophora. This organism is a member of a well-known group of Ascomycetes some of which were discovered as early as 1866. There has been and continues to be considerable controversy as to their taxonomic placement, specifically at the ordinal and family levels. When our isolate, SC15017 was directly compared with the type culture of *Pycnidiophora dispersa* (Clum, 1955) they were found to be identical. The description also matches that of the organism reported in the Japanese Patent 18952 in which the name *Westerdykella dispersa* was used; that assignment was based on their comparison with *W. dispersa* IFO strain 8431, however, the IFO strain was not the original Clum strain. These organisms all share the following characteristics:

1) the sexual fruiting body is a true cleistothecium with a discrete peridium;
2) The asci have a single layered wall;
3) the ascospores are free with up to 32 per ascus rather than disarticulated segments of eight 4-celled ascospores;
4) the asexual stage is pycnidial.

The data presented here forms the basis for the identification of SC15017 as *Pycnidiophora dispersa* sensu Clum (1955) and the designation of *Westerdykella dispersa* as a synonym. *Pycnidiophora dispersa* (Clum) is recognized by Thompson & Backus (1966) and supported by Mukerji & Saksena (1975).

The Antibiotic Lanomycin Ib and Compound Ic

The antibiotics lanomycin and the natural product Ic can be produced by cultivating cnoora sersa, A.T.C.C. No. 74,021 at, or near, 25° C. under submerged aerobic conditions in an aqueous nutrient medium containing assimilable carbohydrate and nitrogen sources. The fermentation is carried out until substantial activity is imparted to the medium, usually about 72 to 76 hours.

After three days the broths are pooled and filtered. The cell mass is extracted with ethyl acetate and the concentrated ethyl acetate extract is chromatographed on silica gel eluting with a heptane-ethyl acetate-methanol step gradient. Final purification of the active fractions from the silica gel column is achieved using an Ito counter current chromatography oil with a heptane-chloroform-methanol buffer system. The above-described methodology for the production of lanomycin is new and is considered a part of the present invention.

The Natural Product of Formula IIb

The compound of IIb, which is the alcohol derivative of Ib and Ic, can be readily obtained by treating the lanomycin fermentation broth with a base, e.g., sodium bicarbonate, and thereafter employing the isolation methodology described above. Alternatively, the semi-synthetic route to prepare IIb, as described above, entails treating either of natural products Ib or Ic with a base to provide the alcohol.

The natural and synthetic compounds of formula I and pharmaceutically acceptable salts thereof, can be used to combat fungal infections (particularly infections of Caa and other yeasts and filamentous fungi, such as Tricophyton, Microsporum, etc.) in domesticated animals and humans. In addition, these compounds have been found to inhibit cytochrome P450 enzymes, such as lanosterol demethylase. These compounds can therefore be used in a variety of ways including as an adrenal steroidogenesis inhibitor for the treatment of metastatic mammary carcinoma, in post-menopausal or ovariectomized women, in Cushing's syndrome, in breast, prostatic, endometrial, ovarian and pancreatic carcinomas, and as an inhibitor of aromatase or other cytochrome P450 enzymes. Based on this cytochrome P450 inhibition activity, the compounds of the present invention are also expected to be useful in the treatment of hypertension. These compounds can be administered topically, orally or parenterally The dosage used of scopularin, a pharmaceutically acceptable salt thereof, or the alcohol derivative thereof will vary with the severity of the infection or disorder and the size of the host. For a human adult, daily doses of about 100 mg to 1 gm/day are exemplary. Information relating to the potency of scopularin and its alcohol derivative is set forth below under the heading "Biological Activity".

Compounds of formula I, or salts thereof, may also be used in the treatment of fungal diseases of plants and may be used as plant growth regulators by inhibition of cytochrome P450 monooxygenases involved in the biosynthesis of gibberellin. Treatment with the compounds of formula I for these uses may be carried out by application to seed, foliage or to the soil.

The following examples further illustrate the preparation and utility of the natural and synthetic products of the present invention.

EXAMPLE 1

Scopulariopsis sp. A.T.C.C. No. 20,914 was maintained on the following sterilized agar medium (A):

| Malt Extract | 10.0 g |
| Yeast Extract | 10.0 g |
| Peptone | 1.0 g |
| Dextrose | 20.0 g |
| Agar | 15.0 g |
| Distilled Water to | 1000 ml |

The pH was adjusted to 7.0 and the medium was sterilized at 121° C. for 20 minutes.

A loopful of surface growth from agar slants (Medium A) of Scopulariopsis sp. was used to inoculate each of five 500ml Erlenmeyer flasks each containing 100 ml of the following sterilized medium (B):

| Toasted Nutrisoy Flour | 15.0 g |
| Soluble Starch | 15.0 g |
| Glucose | 50.0 g |
| $CoCl_2.6H_2O$ | 0.005 g |
| $CaCO_3$ | 10.0 g |
| Distilled Water to | 1000 ml |

After inoculation, the flasks were incubated at 25° C. on a rotary shaker (300rpm; 2 inch stroke) for approximately 72 hours with a resulting broth pH 6.0–6.5. Transfers of 4% (vol./vol.) were made from the grown culture flasks to one hundred 500 ml Erlenmeyer flasks each containing 100 ml of sterilized medium C: (Medium C was Medium A described above without the addition of agar). After inoculation, the flasks were once again incubated at 25° C. on a rotary shaker (as previously described) for approximately 72 hours with a resulting broth pH of 6.0–6.5. At this time, the contents of the flasks were pooled and the broth was filtered. The cell mass (2.0 kg) obtained was extracted twice with 2 L portions of methanol (1 hour for each extraction) and the extract concentrate (ca. 4.5×) was isolated.

Examples 2 and 3, which follow, outline typical isolation techniques used for isolation of Scopularin after fermentation as described above.

EXAMPLE 2

After the fermentation was completed, the pooled whole broth was filtered and the cell cake, consisting of 500 mL of wet cells, was extracted with 2×1 L portions of methanol, stirring the suspension for one hour with each pass. The combined methanol extracts were concentrated to 100 mL and this aqueous residue was lyophilized. The resulting oil was redissolved in a minimum of methanol and applied to the head of a 2.5×15 cm column packed with Merck silica gel and equilibrated with heptane. The column was eluted with 2 L of ethyl acetate/heptane (1:9) followed by 1 L portions of methanol/chloroform (1:200) followed by (1:100) followed by (1:50). Twenty five mL fractions were collected and assayed by TLC. (TLC $R_f$ of 0.4 on E. Merck Kieselgel 60 $F_{254}$ 5×10 cm plates with a methanol-chloroform (1:19) solvent system). Fractions containing Scopularin by TLC were pooled and the solvent removed. The active fraction from the silica gel column was loaded onto the head of an Ito Multi-Layer Coil Separator-Extractor (P. C. Inc., Potomac, Md.) which was filled with the lower phase of a heptane/ethyl acetate/methanol/buffer (0.1M ammonium acetate adjusted to pH 4.5 with acetic acid) (1:1:1:1) system. The coil, a multilayer teflon tubing (1.6 mm, i.d.) with a volume of 330 mL, was spun at 800 rpm and the upper phase of the solvent system was pumped through the coil at 4 mL/min. and collected in 5 minute fractions. Pure scopularin eluted in fractions 32–46. These fractions were pooled and the solvent evaporated to yield 15 mg of pure ($2\alpha$, $3\beta$, $4\alpha$, $5\alpha$)-Tetrahydro-4-methoxy-5-methyl-2-(1-methyl-1,3,5-nonatrienyl)-2H-pyran-3-ol, aminoacetate ester.

The pooled whole broth from a 10 L fermentation was extracted with 2, five L portions of ethyl acetate and the combined organic layers were concentrated to an oil and taken up in a small volume of methanol for storage in a freezer. The extracts from five 10 L batches were pooled and concentrated to an oily residue and this residue re-dissolved in 100 mL methanol. Fifty mL of the pooled extract was shaken with an additional 50 mL methanol and 250 mL ethyl acetate and 250 mL water. After removal of the aqueous layer, the organic phase was re-extracted with two additional 250 mL portions of lower phase from the ethyl acetate/methanol/water (5:2:5) solvent mixture. The combined aqueous phases were concentrated to approximately 100 mL vacuo and extracted with 3×100 mL portions of ethyl acetate. The combined ethyl acetate phases were concentrated to dryness. The above extraction procedure was performed on the remaining 50 mL of methanol concentrate and the final ethyl acetate concentrates were combined. This material was purified using the Ito and silica gel steps as given above to yield 70 mg pure scopularin.

The following example illustrates synthesis of the alcohol derivative of scopularin.

EXAMPLE 4

Alcohol Derivative of Scopularin

The alcohol of scopularin is easily prepared from scopularin by basic hydrolysis of its ester linkage. For example, 60 mg of scopularin was dissolved in 2 mL methanol. 1 mL of saturated, sodium carbonate solution was added and the mixture was allowed to stir. After 2 hours the reaction was complete as judged by TLC. (The alcohol has an $R_f$ of 0.4 on Merck silica gel plates, using ethyl acetate/heptane (2:3) as the developing solvent, and may be visualized using short wave ultraviolet light, $I_2$, phosphomolybdic acid, vanillin/$H_2SO_4$, and other reagents sensitive to olefins and hydroxyl groups.) The mixture was diluted with 20 mL $H_2O$ and the resulting solution was extracted three times with 50 mL portions of dichloromethane. The combined organic extracts were dried over sodium sulfate, concentrated and chromatographed on a 20 g silica gel column using ethyl acetate/heptane (15:85) as the eluting solvent. Five mL fractions were collected and examined by TLC. Fractions containing pure alcohol were pooled and the solvent evaporated to yield 40 mg, 80% of the theoretical yield of scopularin alcohol.

Figure 6:
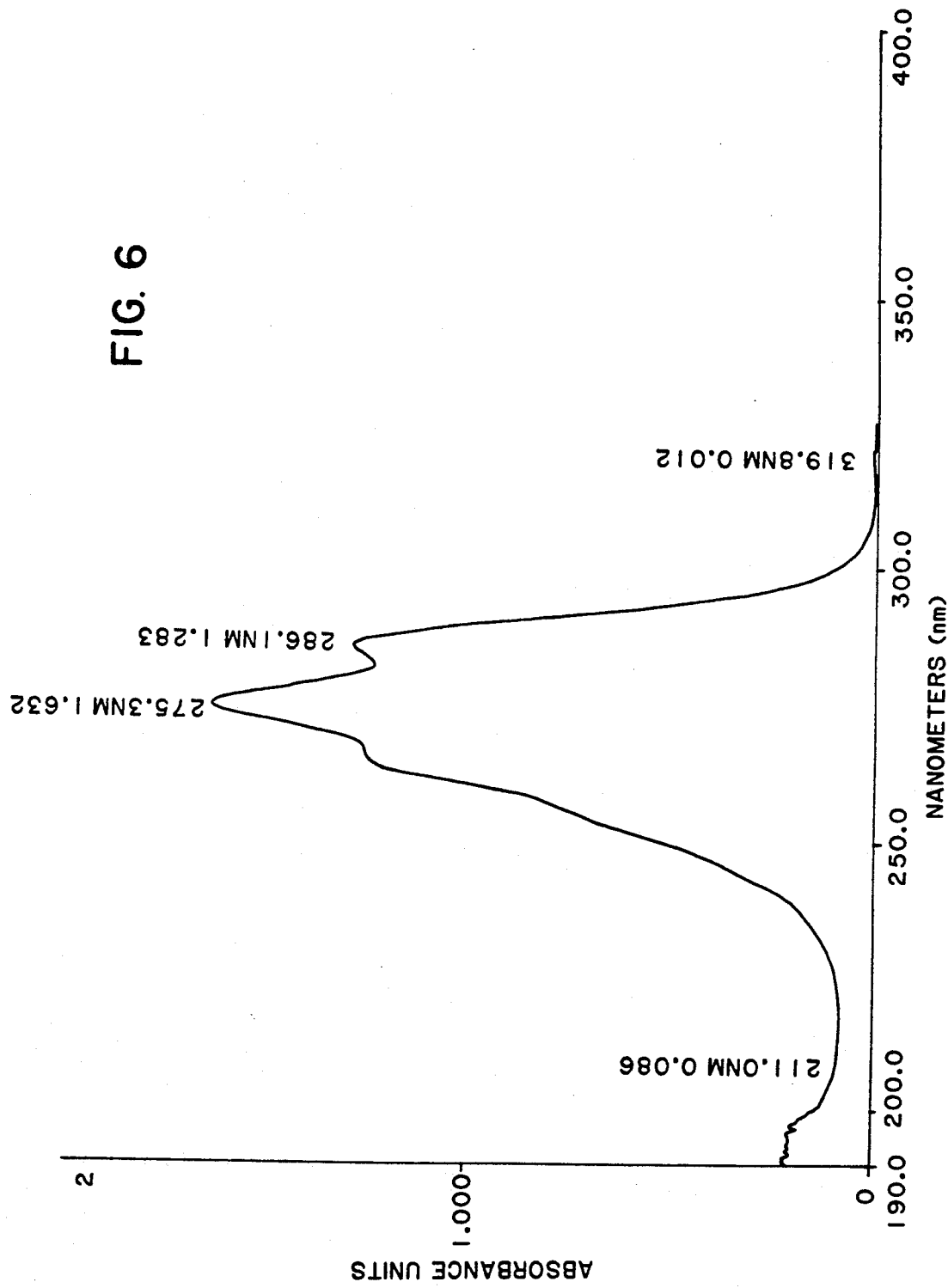
FIG. 6 is the ultraviolet spectrum of scopularin alcohol recorded in methanol.
Figure 7:
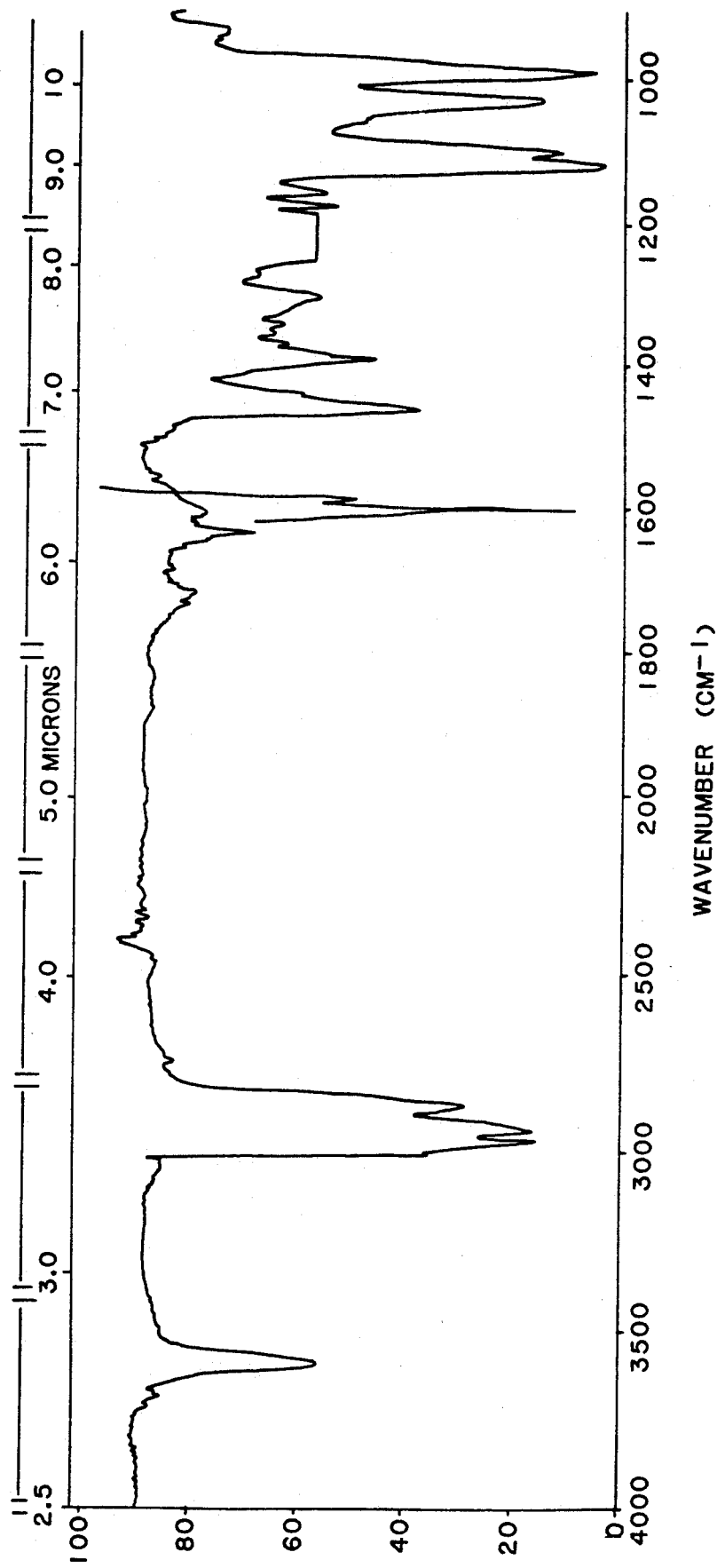
FIG. 7 is the infrared spectrum of scopularin alcohol recorded in chloroform.
Figure 8:
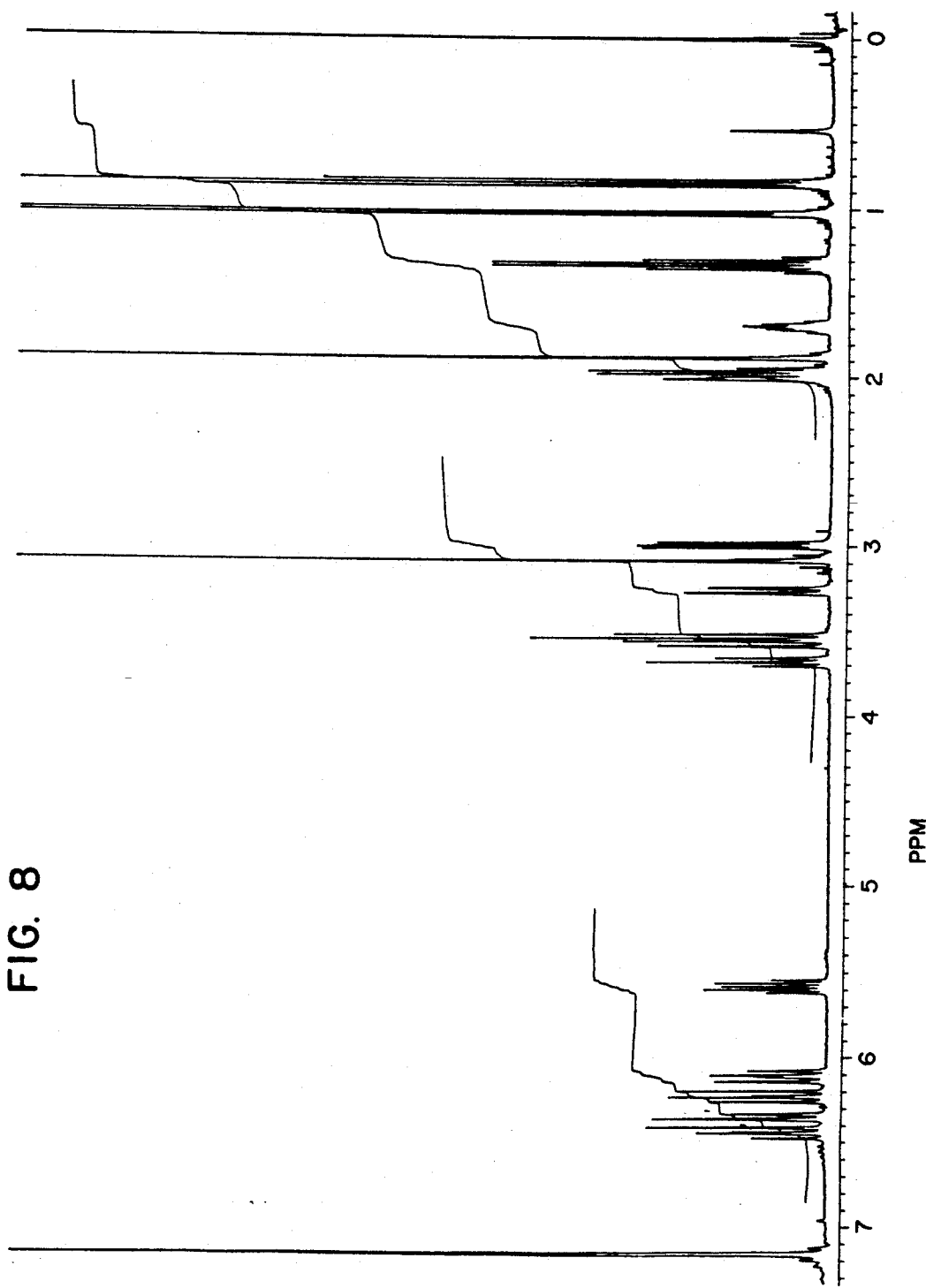
FIG. 8 is the 400 MHz $^1$H NMR spectrum of scopularin alcohol recorded in deuterobenzene.

The alcohol has the following spectral properties: The ultraviolet spectrum, shown in FIG. 6, is superimposable on the spectrum of scopularin, containing a maximum absorbance at 275 nm ($\epsilon$max 40,000), with shoulders at 266 and 286 nm. The infrared spectrum contains absorptions at 3590, 2970, 2940, 2860, 1460, 1390, 1115, 1095, 1025, 990 cm$^{-1}$. The infrared spectrum of the alcohol is shown in FIG. 7. The positive ion CI mass spectrum (not shown), contains ions consistent with the proposed molecular weight of 280 daltons, i.e. m/z 281=[M+H]$^+$, 280=[M+H-H·]$^+$ and 279=[M+H-H$_2$]$^+$. Other ions in the spectrum correspond to losses of methanol and water from the pseudomolecular ion cluster. A high resolution mass measurement of the m/z 279 ion was consistent with the composition  $C_{17}H_{27}O_3$. 279=[M+H-H$_2$]$^+$=279.1965; theoretical=279.1960. This result suggests the formula $C_{17}H_{29}O_3$ for the neutral molecule. The 400 MHz $^1$H NMR spectrum of the alcohol, recorded in deuterobenzene is shown in FIG. 8. The 67 MHz $^{13}$C NMR spectrum (not shown) recorded in the same solvent contained the following resonances (ppm relative to internal TMS) 135.06, 34.77, 134.02, 131.66, 129.30, 126.97, 87.11, 4.92, 71.01, 68.65, 56.10, 35.22, 32.40, 22.84, 3.82, 11.14.

EXAMPLE 5

*Pycnidiophora dispersa*, A.T.C.C. No. 74,021 was maintained on the following sterilized agar medium:

| Medium A | |
|---|---|
| Malt Extract | 10.0 g |
| Yeast Extract | 10.0 g |
| Peptone | 1.0 g |
| Dextrose | 20.0 g |
| Agar | 15.0 g |
| Distilled Water to | 1000 ml |

The pH was adjusted to 7.0 and the medium was sterilized at 121° C. for 20 minutes.

Seed cultures were prepared by transferring a loopful of surface growth from an agar slant culture of *P. dispersa* SC15017 (A.T.C.C. 74,021) into 500 ml Erlenmeyer flasks containing 100 ml of sterilized medium. The medium contained toasted nutrisoy flour, 1.5%, soluble starch, 1.5%, glucose, 5%, CoCl$_2$·6H$_2$O, 0.0005%, CaCO$_3$, 1% and distilled water. Inoculated flasks were incubated at 25° C. on a rotary shaker (300 rpm; 5 cm stroke) for approximately 72 hours. A 5% transfer of this culture was then made to Erlenmeyer flasks each containing 100 ml of the following medium: glucose, 2.5%, yeast extract, 0.2%, N-Z amine A, 0.4%, $K_2HPO_{4b}$, 0.1%, $NaH_2PO_4 \cdot H_2O$, 0.1%, NHCl, 0.05%, $MgSO_4 \cdot 7H_2O$, 0.02% and distilled water. The pH was adjusted to 7. Flasks were incubated at 25° C. on a rotary shaker at 300 rpm as before. At about 48 hours flasks were harvested by filtration through celite.

The following example outlines the typical isolation technique for isolation of lanomycin Ib and the natural product of formula Ic after fermentation as described above.

EXAMPLE 6

Isolation of Lanomycin of Formula Ib and Natural Product of Formula Ic

The culture beer (10 L fermentation) was filtered and the cells discarded. The filtrate was extracted twice with ½ volumes of ethyl acetate. The combined organic layers were concentrated to give 1.40 g of a brownish oil. This sample was split and 700 mg subjected to countercurrent chromatography in heptane-ethyl acetate-methanol—pH 4.5, 0.1M $NH_4OAc$ buffer (1:2:1:2), organic phase mobile using a high-speed countercurrent chromatograph, (P. C. Inc., Potomac, Md., U.S.A.) operated at 800 rpm using a 330 ml volume multilayer Teflon tube (1.6 mm i.d.). This yielded lanomycin of formula Ib, 100 mg, sufficiently pure for spectroscopy and chemical degradation. The second compound was not recovered from this purification, however, and in subsequent workups, the oil was first chromatographed on a 3.0×25 cm bed of silica gel eluted with increasing concentrations of methanol in chloroform to give a fraction containing mostly lanomycin and another more polar band, containing compound Ic. Lanomycin was then purified using the Ito coil as described above while compound Ic was chromatographed using a 1.5×20 cm column of LH-20 and heptane-chloroform-methanol 10:10:1 as the eluant. All of the impurities, co-chromatographing with compound Ic on the silica gel chromatography eluted in one or two column volumes on the LH-20 column while compound Ic eluted quite pure in a very broad band centered at 6 to 7 column volumes.

Lanomycin $2\alpha,3\beta,4\alpha 5\alpha$)-Tetrahydro-4-methoxy-5-methyl-2-(1methyl-1,3,5-heptatrienyl)-2H-pyran-3-ol, amino-acetate ester.

Slightly yellow oil, $[\alpha]_D+°$(c, MeOH); TLC ($CHCl_2$—$CH_3OH$, 19:1) $R_f$ 0.45; UV in $CH_3OH$, $\lambda_{max}$ (logε), 266(4.25) 273(4.37), 284(4.27), IR ($CHCl_3$) $cm^{-1}$, 2960, 2920, 2840, 1735, 1700, 1610, 1440, 1380, 1110, 1025, 980. MS/HRMS, positive ion $CI\{CH_4/N_2O\}$, m/z. HRFAB vs. PEG 310 $[M+H]+$, 270, 253, 235, 203. Measured 310.2025; $C_{17}H_{28}NO_4=310.2018$.

Antibiotic Ic 2a,3b,4a,5a)-Tetrahydro-4-methoxy-5-methyl-2-(1methyl-1,3,5-heptatrienyl)-2H-pyran-3-ol, (b-Dglucopyranosyl amino) acetate ester $[\alpha]_D+°$(c, MeOH); TLC ($CHCl_3$—$CH_3OH$, 10:1) $R_f$ 0.15; UV in $CH_3OH$, $\lambda_{max}$ (logε), 266(4.42) 273(4.53), 284(4.43), IR ($CHCl_3$) $cm^{-1}$, 3420 (br), 2980, 2920, 2860, 1740, 1460, 1390, 1115, 1030, 990. MS/HRMS, positive ion $CI\{CH_4/N_2O\}$, m/z. HRFAB vs. PEG 472 $[M+H]+$, 310, 253, 235. Measured=472.2577; $C_{23}H_{38}NO_9=472.25$.

EXAMPLE 7

($2\alpha,3\beta,4\alpha,5\alpha$)-Tetrahydro-4-methoxy-5-methyl-2-(1-methylnonyl)-2H-pyran-3-ol To the title compound of Example 4 (35 mg, 0.13 mMole), dissolved in 5 mL of methanol was added 5 mg of 10% palladium on carbon. The flask was evacuated and flushed with nitrogen gas three times before being charged with hydrogen gas. The mixture was allowed to stir at 25° C. for 5 hours. The mixture was filtered through celite and the solvent removed to provide 29.5 mg of the title compound. Proton and carbon NMR showed a two to one mixture of diastereomers. MS; +CI $[M+H]+=m/z$ 287, $[M-H]^-=m/z$ 285. $R_f=0.79$ in EtOAc-Heptane (1:1).

EXAMPLE 8

Glycine, $2\alpha,3\beta,4\alpha,5\alpha$)-tetrahydro-4-methoxy-5-methyl-2-(1-methylnonyl)-2H-pyran-3-yl ester The title compound of Example 7 (24 mg, 0.084 mMole) was reacted with 3 eq. each of N-α-BOC-glycine (44 mg, 0.25 mMole) and dicyclohexylcarbodiimide (52 mg, 0.25 mMole) plus 10 mg of dimethylaminopyridine in 3 mL of dry tetrahydrofuran. This mixture was allowed to stir under argon for 3 hours at 25° C., filtered and the filtrate taken to dryness. Chromatography on silicon oxide (EtOAc/Heptane 15:85) pooling the fractions gave 40 mg (0.10 mMole) of the BOC protected glycyl ester.

The entire sample from above was dissolved in formic acid and the solution allowed to stand at room temperature for 30 minutes. Two mL of toluene was added and the mixture was taken to dryness. The oil was immediately chromatographed on silicon oxide using $CHCl_3/MeOH$ (97:3). The pooled fractions contained 14.7 mg of the title compound. MS; +CI $[M]+=m/z$ 343. $R_f=0.38$ in $CHCl_3/MeOH$ (95:5).

EXAMPLE 9

($2\alpha,3\beta,4\alpha,5\alpha$)-Tetrahydro-4-methoxy-5-methyl-2-(1-methyl-1,3,5-heptatrienyl)-2H-pyran-3-ol The entire sample (680 mg) of an ethyl acetate extract concentrate from an alkaline (pH 8) fermentation filtrate, the fermentation of which is described in Example 5, was loaded in 3 mL of chloroform onto the head of a 100 g silicon oxide column (bed volume 25×450 mm) which had been equilibrated with 0.75% methanol/chloroform. After loading flow of 0.75% methanol/chloroform was maintained at 4 mL/min. and 5 mL fractions were collected. Fractions 66 through 69 contained the title compound. These fractions were pooled and the solvent evaporated to yield 20 mg of the pure alcohol.

EXAMPLE 10

β-Alanine,
[2S-[2α(E,E,E),3β,4α,5α]]tetrahydro-4-methoxy-5-methyl-2-(1-methyl-1,3,5-heptatrienyl)-2H-pyran-3-yl ester A. 3-[[(1,1-Dimethylethoxy)carbonyl]amino]-propanoic acid,
2S-[2α(E,E,E),3β,4α,5α]]-tetrahydro-4-methoxy-5-methyl-2-(1-methyl-1,3,5-heptatrienyl)-2H-pyran-3-yl ester To 50 mg of the title compound of Example 9 (0.2 mMole) and dicyclohexylcarbodiimide (83 mg, 0.4 mMole) and butyloxycarbonyl-β-alanine (76 mg, 0.4 mMole) in 10 mL tetrahydrofuran under argon atmosphere, at 0° C., was added 5 mg DMAP in ca. 20 μL tetrahydrofuran. The reaction was allowed to warm to 25° overnight. In the morning an additional (0.4 mMole) of dicyclohexylcarbodiimide and the carboxylic acid were added. This mixture was stirred for an hour, filtered and chromatographed on 20 g silica gel (20 mm id) with 15% ethyl acetate/heptane as the eluting solvent. Appropriate fractions (by TLC, 40% ethyl acetate/heptane) were pooled to yield (37 mg, 0.09 mMole) of the title A compound.

B. β-Alanine,
[2S-[2α(E,E,E),3β,4α,5α]]-tetrahydro-4-methoxy-5-methyl-2-(1-methyl-1,3,5-heptatrienyl)-2H-pyran-3-yl ester Formic acid (2 mL) was used to dissolve and deprotect the title A compound (37 mg, 0.09 mMole). After 35 minutes at 25° C., the solution was diluted with water and adjusted to pH 7 by careful addition of concentrated ammonium hydroxide. The resulting solution was extracted with 3×25 mL portions of ethyl acetate and the organic layers combined and dried over sodium sulfate. After filtration the solvent was removed. The residue was chromatographed using a Pasteur pipette column ½ filled with silica gel. Elution with 5% methanol/chloroform gave the pure title product (17 mg, 0.05 mMole).

EXAMPLE 11

1H-Imidazole-1-acetic acid,
[2α(E,E,E),3β,4α,5α]-tetrahydro-4-methoxy-5-methyl-2-(1-methyl-1,3,5-heptatrienyl)-2H-pyran-3-yl ester The title compound of Example 9 (100 mg, 0.4 mMole), bromoacetic acid (111 mg, 0.8 mMole, 2 eq.), dicyclohexylcarbodiimide (164 mg, 0.8 mMole, 2 eq.) plus a few crystals of dimethylamino-pyridine were dissolved in 5 mL of freshly distilled tetrahydrofuran and the resulting solution was stirred for 1.5 hours at 25° C. The mixture was filtered, taken to dryness and chromatographed on silicon oxide (EtOAc/Heptane 1:9) and fractions containing pure product were pooled and the solvent removed to yield 136.7 mg (0.37 mMole) of the bromoacetate intermediate.

This intermediate (120 mg, 0.32 mMole) was combined with imidazole (46 mg, 0.67 mMole, 2.1 eq.) and sodium iodide (53 mg, 0.35 mMole, 1.1 eq.) and the mixture was dissolved in 2 mL of freshly distilled acetonitrile. The solution was heated to reflux for 60 minutes. The reaction was cooled and filtered and 2 mL water was added to the filtrate and the mixture was shaken with 3×3 mL volumes of ethyl acetate. The ethyl acetate layers were combined and evaporated and the crude product was purified by chromatography on silicon oxide. Fractions shown to contain pure product were pooled and after evaporation of the solvent yielded 59 mg (0.16 mMole) of the title compound. MS+CI [M+H]+=m/z 361. $R_f$=0.37 in CHCl$_3$/MeOH 9:1.

EXAMPLE 12

3-Aminopropanoic acid,
[2α(E,E,E),3β,4α,5α]-tetrahydro-4-methoxy-5-methyl-2-(1-methyl-1,3,5-non-atrienyl)-2H-pyran-3-yl ester Using the procedure of Example 8, but substituting N-α-BOC-3-aminopropanoic acid for the protected glycine of Example 8, the title compound was prepared. $R_f$=0.5 in CHCl$_3$/MeOH 4:1. MS; +CI [M+H]+=m/z 352.

EXAMPLE 13

4-Aminobutanoic acid,
[2α(E,E,E),3β,4α,5α]-tetrahydro-4-methoxy-5-methyl-2-(1-methyl-1,3,5-non-atrienyl)-2H-pyran-3-yl ester Using the procedure of Example 8, but substituting N-α-BOC-4-aminopropanoic acid for the protected glycine of Example 8, the title compound was prepared. $R_f$=0.2 in CHCl$_3$/MeOH 4:1. MS; +CI [M+H]+=m/z 366.

EXAMPLE 14

(2α,3β,4α,5α)-2-[Tetrahydro-4-methoxy-5-methyl-2-(1-methylnonyl)-2H-pyran-3-yl]oxy]ethanol To 100 mg (0.39 mMole) of the title compound of Example 7 in 3 mL of dry methylene chloride a few mg of Rh(OAc)$_2$ was added together with 100 μL (0.95 mMole) of ethyl diazoacetate and the resulting mixture allowed to stir at 25° C. for one hour. The reaction mixture was then added to 2 mL of water and the resulting solution extracted with 3×2 mL portions of dichloromethane. The combined organic layers were taken to dryness and the oil chromatographed on silicon oxide eluting with ethyl acetate/heptane 5/95. The resulting ether esters (TLC, EtOAc/Heptane 1:9, $R_f$=0.22 and 0.18), diastereomeric at the alaphatic side-chain methyl, were used as a mixture of isomers without additional purification.

The ether esters from above (95 mg, 0.25 mMole) were dissolved in 1 mL dry tetrahydrofuran under argon and an excess of lithium aluminum hydride was added. The slurry was stirred for 10 minutes. Water was added dropwise to decompose the unreacted lithium aluminum hydride and when no foaming occurred on addition of a drop an additional 3 mL of water was added. The aqueous mixture was extracted with 3×5 mL portions of ethyl acetate and the combined organic extracts washed with 2 mL of water, the solvent removed and the resulting oil pumped on under high vacuum giving 64 mg (0.19 mMole) of the title product. MS; +CI [M+H]+ =m/z 331. $R_f$=0.14. EtOAc/Heptane 4:6.

(2α,3β,4α,5α)-2-[[Tetrahydro-4-methoxy-5-methyl-2-(1-methylnonyl)-2H-pyran-3-yl]oxy]ethanamine A solution of the title alcohol of Example 14 (53 mg, 0.16 mMole) in 5 mL of dichloromethane was treated with 2 eq. of tosyl chloride and 2.1 equivalents of dimethylaminopropylene. The resulting mixture was stirred for 10 minutes under argon, then sealed and transferred to a 5° C. cold room overnight. The mixture was diluted wiht 3 mL of water and extracted with 3×3 mL of dichloromethane. The solvent was removed from the combined organic layers and the resulting oil was purified by chromatography on silicon oxide using ethyl acetate/heptane 15/85. The tosylate recovered from the column (87 mg, 0.18 mMole) has a TLC $R_f$ of 0.43 (EtOAc/Heptane 3:7), and MS; +CI [M+H]+ =m/z 485.

A portion of the tosylate from above (34 mg, 0.07 mMole) was dissolved in 2 mL of dimethylformamide and 23 mg of $NaN_3$ in 0.3 mL water was added. This mixture was heated to 65° C. for two hours at which time chromatography ($R_f$ of azide=0.68, $SiO_2$, EtOAc/Heptane 3:7) showed the absence of starting material. The mixture was added to 5 mL water and the aqueous solution was extracted with 3×5 mL portions of ether. The combined ether layers were reduced to dryness then redissolved in 3 mL dry ether and an excess of lithium aluminum hydride was added. This mixture was allowed to stir overnight under argon atmosphere at 25° C., after which time chromatography showed no starting material remaining. Water was added to decompose the unreacted lithium aluminum hydride and when no foaming occurred on addition of a drop an additional 3 mL of water was added. The layers separated and the aqueous layer was extracted with an additional 2×3 mL portions of ethyl ether. The combined ether layers were taken to dryness and the resulting oil chromatographed on HP-20 employing a linear gradient from $CHCl_3$/MeOH 8:2 to MeOH. Pooling and concentration of appropriate fractions gave 14.7 mg (0.045 mMole of the title amine ether. TLC $R_f$=0.28, $CHCl_3$/MeOH, 4:1; MS; +CI [M+H]+ =m/z 330.

EXAMPLE 16

(2α,3β,4α,5α)-2-[[Tetrahydro-4-methoxy-5-methyl-2-(1-methylnonyl)-2H-pyran-3-yl]oxy]ethanethiol To 23 mg of the tosylate from Example 15 (0.047 mMole) dissolved in 3 mL ethanol was added 23.8 mg potassium thioacetate, a reflux condenser was then fitted and the flask heated to 65° C. for ca 2 hours at which time chromatography ($R_f$ of thioacetate=0.60, $SiO_2$, EtOAc/Heptane 3:7) showed the absence of starting material. The mixture was filtered, the solids triturated with ethyl ether, and the remaining solids dissolved in 2 mL water and the solution extracted with 2×3 mL ethyl ether. The filtrate and all ether fractions were combined and taken to dryness. The thioacetate was hydrolyzed by dissolving the residue in 2 mL of cold 5% methanolic potassium hydroxide and this solution was stirred overnight at 25° C. 1N Hydrochloric acid was added until the solution was acid to pH paper and the methanol was removed. The residue was dissovled in 3 mL water and extracted with 3×3 mL of ethyl ether. The combined ether layers were washed with 1 mL of 1M sodium carbonate and 1 mL water. After removal of the ether 8.2 mg (0.23 mMole) of the title compound remained. TLC $R_f$'s=0.67 and 0.58, EtOAc/Heptane, 3:7; MS; +/−CI[M+H]+ =m/z 347, [M−H]− =m/z 345.

EXAMPLE 17

(2α,3β,4α,5α)-Tetrahydro-4-methoxy-5-methyl-2-(1-methylnonyl)-2H-pyran-3-yl]oxy]acetic acid To 25.7 mg (0.07 mMole) of the ether ester of Example 14 in 1 mL of methanol was added 1 mL of 5% potassium hydroxide in methanol. This solution was stirred for 4 hours at 25° C. at which time chromatography indicated that hydrolysis was complete. The solution was neutralized by addition of 1N hydroOhloric acid (with monitoring by pH paper) and the solvents removed. The residue was dissolved in 2 mL of water and this solution was extracted with 3×2 mL portions of ethyl acetate. The combined ethyl acetate layers were evaporated to dryness leaving 21.6 mg of the title compound. TLC $R_f$=0.14, Toluene/Methanol, 9:1; MS; +CI [M+H]+ =m/z 345, [M+NH_4]+ =m/z 362).

EXAMPLE 18

(2α,3β,4α,5α)-2-[[Tetrahydro-4-methoxy-5-methyl-1-(1-methylnonyl)-2H-pyran-3-yl]oxy]acetamide 18.7 mg (0.05 mMole) of the ether ester from Example 14 was dissolved in 1 mL of isopropanol and 1 mL of concentrated ammonium hydroxide was added. The reaction mixture was maintained at 25° for 2.5 hours then heated at 37° C. for an additional 1.5 hours. AT this time, chromatography indicated absence of starting material, and the solvents were removed. The residue was chromatographed on silicon oxide using Toluene/Methanol 9:1 as the eluting solvent. In addition to 3.4 mg of the starting ester and 1.8 mg of the title compound of Example 17, which were also recovered from the column, pure title compound (10.7 mg, 0.03 mMole) was obtained. TLC $R_f$=0.2, Toluene/Methanol, 9:1; MS; +CI [M+H]+ =m/z 344.

EXAMPLE 19

N-Methylglycine, [2S-[2α(E,E,E),3β,4α,5α]]-Tetrahydro-4-methoxy-5-methyl-2-(1,3,5-nonatrienyl)-2H-pyran-3-yl ester A.
[[(1,1-Dimethylethoxy)carbonyl]methylamino]-acetic acid, [2S-[2α(E,E,E),3β,4α,5α]]-tetrahydro-4-methoxy-5-methyl-2-(1-methyl-1,3,5-nonatrienyl)-2H-pyran-3-yl ester To the alcohol of Example 4 (50 mg, 0.21 mMole) was added 113 mg, 0.6 mMole of [[(1,1 -dimethylethoxy)carbonyl]methylamino]acetic acid, 124 mg, 0.6 mMole dicyclohexylcarbodiimide and ca. 10 mg of dimethylaminopropylene. This mixture was maintained under an argon atmosphere with stirring while 5 mL dry dichloromethane was added. After stirring at 25° for 2 hours, TLC (50% ethyl acetate/heptane) showed that the reaction was complete. Solvent was evaporated and the residue sorbed on a small quantity of silica gel. This material was then placed on a silica column (20 g, 20 mm id.) pre equilibrated with 20% ethyl acetate/heptane. The column was eluted with the equilibrating solvent and pooling of the column fractions was guided by TLC as above. Solvent was evaporated from the pooled fractions containing pure product to leave 80 mg (0.177 mMole) of the title A compound.

B. N-Methylglycine, [2S-2α(E,E,E),3β,4α,5α]]-Tetrahydro-4-methoxy-5-methyl-2-(1,3,5-nonatrienyl)-2H-pyran-3-yl ester The entire sample of the title A compound was dissolved in 3 mL formic acid (to which 300 μl anisole had been added) and the resulting solution allowed to stand at 25° for 60 minutes. Toluene was added and the mixture evaporated to dryness to provide 70 m of the title compound.

EXAMPLE 20

[2S-2α(E,E,E),3β,4α,5α)]]-3-[[(1,1-Dimethylethyl)-dimethylsilyl]oxy]tetrahydro-4-methoxy-5-methyl-2-(1-methyl-1,3,5-heptatrienyl)-2H-pyran A 100 mg (0.4 mMole) portion of the title compound from Example 9 was reacted with t-butyldimethylsilyl chloride and imidazole in dry MeCl$_2$ under argon. The mixture was allowed to stir at 25° C. overnight. In the morning the mixture was diluted with ethyl ether and the imidazole filtered off. The residue from the ether concentrate was then filtered through a 20 g plug of silica gel using 10% ethyl ether/pentane as the eluting solvent. Fractions containing UV active material were pooled and the solvent removed to give 100 mg (0.3 mMole) of the title compound

EXAMPLE 21A

[2S-(2α,3β,4α,5α)]-1-[3-[[(1,1-Dimethylethyl)dimethylsilyl]oxy]tetrahydro-4-methoxy-5-methyl-2H-pyran-2-1]-1-ethanone Two 50 mg portions of the title compound of Example 20 (0.3 mMole total) were reacted with ozone at −78° in 25 mL of dichloromethane until the solution remained blue. Portions of one reaction were treated with Me$_2$S, Ph$_3$P, Rainey Ni, Zn/HOAc, standing at 25°. All workup conditions gave the same mixture of products. All mixtures were pooled and chromatographed on a 20 g silica gel column (20 mm id) with 10% ether in pentane. 10 mL fractions were collected and upper fractions yielded 28 mg of the title 21A compound of this Example and lower fractions yielded 45 mg of the title compound of Example 21B.

EXAMPLE 21B

[2S-[2α(E),3β,4α,5α]]-3-[3-[[(1,1-Dimethylethyl)dimethylsilyl]oxy]tetrahydro-4-methoxy-5-methyl-2H-pyran-2yl]-2-butenal The title 21A residue (900 mg, 2.68 mMole) was dissolved in 200 mL dichloromethane and split into two 100 mL portions. Each portion was ozonated at −78° C. until a light blue color appeared in the flask, at which time ozone generation ceased and 2 mL pyridine was added per 100 mL solution. The mixture was stirred and 2 mL dimethyl sulfide was added. The reaction mixture was then allowed to warm slowly to 0° C. After partitioning against saturated copper(II)sulfate, water and drying over sodium sulfate, the organic phase was concentrated and the residue separated on silica gel, (bed dimensions, 200×30 mm) eluting with column with 8% ether/pentane. 20–25 mL fractions were collected after taking a 250 mL forecut. TLC (20% ether/pentane) guided the pooling of fractions. Solvent evaporation from fractions 7–11 yielded 270 mg (0.89 mMole) of the title compound of Example 20 and fractions 30 through 50 yielded the title compound of this Example 21B (150 mg, 0.46 mMole).

EXAMPLE 21C

[2S-[2α(E,E),3β,4α,5α]]-5-[3-[[(1,1-Dimethylethyl)-dimethylsilyl]oxy]tetrahydro-4-methoxy-5-methyl-2H-pyran-2-yl]-2,4-hexadienal A solution of the title compound of Example 20 (806 mg, 2.2 mmol) in dry dichloromethane (80 ml) containing dry pyridine (3.4 ml) was treated at −78° C. with ozone (flow rate of oxygen 20 l/h; 165 mA: 10 min.) until the starting material was nearly consumed (monitored by TLC). The mixture was rinsed with argon and then a solution of triphenylphosphin (580 mg, 2.2 mmol) in dry dichloromethane (20 ml) was added dropwise at −78° C. The mixture was allowed to come slowly to 0° C. and stirring was continued at this temperature (0° C.) for additional 45 minutes. The solution was washed with aqueous buffer solution (pH=4; potassium hydrogen sulfate) and brine, dried over sodium sulfate and evaporated in vacuo to leave an oil which was chromatographed on silica gel eluting with n-pentane/ether. A trace of the title 21A compound was eluated first, then the aldehyde 21B (145 mg, m.p. 52°–53° C.) and finally the desired title 21C compound. Yield: 345 mg, m.p. 43°–45° C.

EXAMPLE 22

Glycine, [2S-[2α(E,E),3β,4α,5α]]-Tetrahydro-4-methoxy-5-methyl-2-(1-methyl-4-phenyl-1-butadienyl-2H-pvran-3-1 ester A.
2S-[2α(E,E),3β,4α,5α]]-3-[[(1,1-Dimethylethyl)dimethylsilyl]oxy]tetrahydro-4-methoxy-5-methyl-2-(1-methyl-4-phenyl-1,3-butadien-yl]-2H-pyran and B.
[2S0[2α(1E,3Z),3β,4α,5α]]-3-[[(1,1-Dimethylethyl)-dimethyl il 1]]tetrahydro-4-methoxy-5-methyl-2-(1-methyl-4-phenyl-1,3-butadien-yl]-2H-pyran To 1200 mg of anhydrous triphenyl benzyl phosphonium chloride stirring in 5 mL dry tetrahydrofuran at −78° was added 1.9 mL of a 1.6 Molar solution of n-butyl lithium. When the addition was complete, the solution was allowed to warm slowly to 25°. The Wittig reagent was then cooled to 0° and 328 mg (1.0 mMole) of the title compound of Example 21B was added. After 2 hours, methanol was added to quench the unreacted anion, the mixture was filtered and the solvents were removed. The resulting oil was chromatographed on a 20 g silicon oxide column using 5% ethyl ether/pentane. Fractions containing product by chromatography were pooled and the solvent evaporated to yield 310 mg (0.77 mMole) of a mixture of phenyl dienes A and B.

C.
[2S-[2α(E,E),3β,4α,5α]]-Tetrahydro-4-methoxy-5-methyl-2-(1-methyl-4-phenyl-1,3-butadien-yl]-2H-pyran-3-ol The mixture of the title A and B dienes from above were separated by chromatography, eluting at 10 mL/minute and collecting 20 mL fractions. Fractions were examined by chromatography and like fractions were pooled. Fractions 19–32 gave 147 mg of the "E,E" diene, and fractions 38–65 gave 133 mg of the "E,Z" isomer with the intervening "mixed" fractions accounting for the remaining weight The "E,E" isomer (130 mg, 0.32 mMole) was dissolved in a small volume of dichloromethane/acetonitrile and sufficient HF/pyridine was added to effect removal of the dimethyltertbutylsilyl protecting group as seen by chromotography. At this point the mixture was washed with an equal volume of saturated copper sulfate solution followed by water. After solvent removal, the crude alcohol was purified by silicon oxide chromatography eluting with alcohol with 30% EtOAc/n-C₇H₁₆ after elution of higher $R_f$ impurities with 4 column volumes of 15% EtOAc/n-C₇H₁₆. Pooling the appropriate column fractions yielded 86 mg (0.30 mMole) of the title C alcohol.

D. [[(1,1-Dimethylethoxy)carbonyl]amino]acetic acid, [2S-[2α(E,E),3β,4α,5α]]-tetrahydro-4-methoxy-5-methyl-2-(1-methyl-4-phenyl-1,3-butadienyl)-2H-pyran-3-yl ester The title C compound (86 mg, 0.30 mMole), after drying under high vacuum overnight, was u mixed with three equivalents each of N-α-BOC-glycine and dicyclohexylcarbodiimide plus 10 mg of dimethylaminopyridine and the mixture was dissolved in 10 mL tetrahydrofuran. After stirring for three hours, no starting material could be detected by chromatography. Solvent was stripped off and the residue was suspended in 20 mL of dichloromethane, filtered and the filtrate chromatographed on silicon oxide eluting the BOC protected amino ester with 20% EtOAc/n-C₇H₁₆. Fractions containing pure product were combined and after removal of solvent, 102 mg (0.23 mMole) of the title D compound remained as a colorless oil.

E. Glycine, [2S-[2α(E,E),3β,4α,5α]]-Tetrahydro-4-methoxy-5-methyl-2-(1-methyl-4-phenyl-1,3-butadienyl)-2H-pyran-3-yl ester The title D compound was treated with 0.5 mL anisole and the mixture dissolved in 5 mL formic acid. The solution was allowed to stand at room temperature for 30 minutes at which time chromatography (5% methanol/chloroform) showed essentially complete removal of the BOC group. Solvents were removed at 30° C. and reduced pressure and the crude product was purified on a 20 g silicon oxide column, 20 mL fractions were collected. After elution of impurities with 500 mL 1% methanol/chloroform and 250 mL 2% methanol/chloroform, the pure product was eluted with 5% methanol/chloroform. The fractions containing pure product were pooled and after evaporation of solvent 50 mg (0.14 mMole) of the title product remained. ¹H NMR (270 MHz, CD₃OD)δ7.5–7.15 (m, 5H), 7.01 (dd, 1H, J=16, 10.5 Hz), 6.56 (d, 1H, J=16 Hz), 6.15 (d, 1H, J=10.5 Hz), 5.05 (dd[t], 1H, 9.4 Hz), 3.80 (dd, 1H, J=12, 2 Hz), 3.65 (br d, 2H, J∼10 Hz), 3.4–3.2(m, 2H), 3.33 (s, 3H), 2.31 (m, 1H), 1.86 (d, 3H, J∼1Hz), 1.08 (d, 3H, J=7 Hz). ¹³C NMR (67.5 MHz, CD₃OD) 6 174.01, 139.05, 136.05, 134.93, 131.04, 129.98×2, 129.00, 127.76×2, 125.54, 86.81, 83.04, 72.10, 71.15, 56.95, 43.99, 34.03, 12.43, 11.39. MS +CI, NH₃ [M+H]⁺ =346.

EXAMPLE 23

Glycine, [2S-[2α(E,Z),3β,4α,5α]]-Tetrahydro-4-methoxy-5-methyl-2-(1-methyl-4-phenyl-1-butadienyl)-2H-pyran-3-yl ester A. [2S-[2α(1E,3Z),3β,4α,5α]]-Tetrahydro-4-methoxy-5-methyl-2-(1-methyl-4-phenyl-1,3-butadien-yl)-2H-pyran-3-ol 140 mg (0.35 mMole) of the A,B mixture from Example 22 was treated with HF/pyridine and after chromatography and pooling of the proper fractions 98 mg (0.34 mMole) of the title A alcohol was obtained.

B. [(1,1-Dimethylethoxy)carbonyl]amino]acetic acid, [2S-[2α(1E,3Z),3β,4α,5α]]-tetrahydro-4-methoxy-5-methyl-2-(1-methyl-4-phenyl-1,3-butadienyl)-2H-pyran-3-yl ester A dicyclohexylcarbodiimide mediated esterification of the title A compound (98 mg, 0.34 mMole) with 3 equivalents of N-α-BOC-glycine afforded 134 mg of the title B BOC protected ester (0.30 mMole).

C Glycine, [2S-[2α(E,Z),3β,4α,5α]]-Tetrahydro-4-methoxy-5-methyl-2-(1-methyl-4-phenyl-1-butadienyl)-2H-pyran-3-yl ester Deprotection of the amino group on the entire sample of the title B compound with formic acid gave 80 mg (0.23 mMole) of the title glycine ester. ¹H NMR (270 MHz, CD₃OD)δ7.4–7.2 (m, 5H), 6.53–6.35 (m, 3H), 5.04 (dd[t], 1H, J=9.4 Hz), 3.78 (dd, 1H, J=12.2 Hz), 3.62 (m, 1H), 3.61 (d, 1H, J=10 Hz), 3.46 (dd, 1H, J=9.4, 5.3 Hz), 3 45–3.2 (m, 2H), 3.32 (s, 3H), 2.30 (m, 1H), 1.83 (d, 3H, J∼1 Hz), 1.06 (d, 3H, J=7 Hz). ¹³C NMR (67.5 MHz, CD₃OD)δ172.37, 138.93, 138.04, 132.28, 130.41×2, 129.66×2, 128.57, 126.84, 126.38, 86.61, 82.89, 72.04, 71.55, 56.89, 43.18, 33.91, 12.40, 11.33. MS+CI, NH₃ [M+H]⁺ =3.46.

EXAMPLE 24

N,N-Dimethylglycine, [2S-[2α(E,E),3β,4α,5α]]-tetrahydro-4-methoxy-5-methyl-2-(1-methyl-1,3,5-heptatrienyl)-2H-pyran-3-yl ester To a solution of the title compound of Example 9 (0.1 g, 0.396 mmol) in methylenechloride (20 ml) was added ethyl-3-(3-dimethylamino) propyl carbodiimide hydrochloride (0.3 g, 1.58 mmol), N,N-dimethyl-glycine (0.16 g, 1.58 mmol) and a catalytic amount of dimethylaminopyridine. The mixture was stirred overnight at room temperature under argon, washed with water and evaporated n vacuo. The crude material was purified by chromatography on silica gel using ethyl acetate as eluent to provide 104 mg of the title compound.

EXAMPLE 25

N-Phenylglycine, [2S-[2α(E,E),3β,4α,5α]]-tetrahydro-4-methoxy-5-methyl-2-(1-methyl-1,3,5-heptatrienyl)-2H-pyran-3-yl ester A. [[(1,1-Dimethylethoxy)carbonyl]phenylamino]acetic acid, [2S-[2a(E,E,E),3β,4α,5α]]-tetrahydro-4-methoxy-5-methyl-2-(1-methyl-4-phenyl-1,3-butadienyl)-2H-pyran-3-yl ester To a solution of the title compound of Example 9 (0.4 g, 1.59 mmol) in methylenechloride (30 ml) was added ethyl-3-(3-dimethylamino) propyl carbodiimide hydrochloride (1.22 g, 6.36 mmol), [[(1,1-dimethylethoxy)carbonyl]phenylamino]acetic acid (1.08 g, 4.3 mmol), and a catalytic amount of dimethylaminopyridine. The mixture was stirred for two hours at room temperature under argon, washed with water and evaporated n vacuo. The crude material was purified two times by chromatography on silica gel using ethyl acetate-hexane (1:2) as eluent to provide 0.176 g of the title A compound.

B. N-Phenylglycine, 2S-[2α(E,E,E),3β,4α,5α]]-tetrahydro-4-methoxy-5-methyl-2-(1-methyl-1,3,5-heptatrienyl)-2H-pyran-3-yl ester The title A compound (0.15 g, 0.31 mmol) was dissolved in formic acid and stirred for 90 minutes at room temperature under argon. The pH was adjusted to 7.2 by the addition of aqueous ammonia and the mixture extracted with ethyl acetate. The organic layer was dried over sodium sulfate and evaporated n vacuo. The crude product was purified by chromatography on silica gel using hexane with an increasing amount of ethyl acetate (0–25) as eluent to provide 25 mg of the title compound.

EXAMPLE 26

Glycine, [2S-[2α(E),3β,4α,5α]]-tetrahydro-4-methoxy-5-methyl-2-(1-methyl-1-heptenyl)-2H-pyran-3-yl ester

A. 2S-[2α(E),3β,4α,5α]]-Tetrahydro-4-methoxy-5-methyl-2-(1-methyl-1-heptenyl]-2H-pyran-3-ol A solution of the title compound of Example 9 (0.51 g, 2.0 mmol) in dry methanol (40 ml) was hydrogenated in the presence of palladium (10%) on carbon (50 mg) and the course of the hydrogenation was monitored by chromatography. After 20 minutes all starting material was consumed and a mixture of perhydrogenated diastereomers and various partial hydrogenated products was present. The hydrogenation was stopped, the catalyst was removed by filtration and the solvent was distilled off n vacuo to leave an oil which was chromatographed on silica gel eluting with ether/petroleum ether (4:1). First fractions (26–32) contained the mixture of perhydrogenated diastereomers (190 mg) whereas 100 mg of the desired mono-ene title A product was obtained from late fractions (55–66) as a colorless oil.

B. [[(1,1-Dimethylethoxy)carbonyl]amino]acetic acid, [2S-[2α(E),3β,4α,5α]]-tetrahydro-4-methoxy-5-methyl-2-(1-methyl-1-heptenyl)-2H-pyran-3-yl ester To a solution of title A compound (100 mg, 0.39 mmol) in dry dichloromethane (5 ml) was added successively 1-ethyl-3-(3-dimethylaminopropyl)-carbodiimide hydrochloride (299 mg, 1.56 mmol), 4-dimethylaminopyridine (few mg, catalytic amount) and N-BOC-glycine (273 mg, 1.56 mmol). The mixture was stirred at room temperature for 4.5 hours and then washed twice with water. The organic phase was dried over sodium sulfate, evaporated in vacuo to leave an oil (310 mg) which was purified by chromatography on silica gel eluting with ether/pentate (1:1). Appropriate fractions were pooled to yield 110 mg of the title B compound as a colorless oil.

C. Glycine, [2S-[2α(E),3β,4α,5α]]-tetrahydro-4-methoxy-5-methyl-2-(1-methyl-1-heptenyl)-2H-pyran-3-yl ester The solution of the title B compound (100 mg, 0.24 mmol) in concentrated formic acid (5 ml) was stirred at room temperature for 50 minutes (monitored by chromatography) and then cooled to 0° C. Ice-water (10 ml) was added slowly and the pH was adjusted to 7 by addition of concentrated ammonium hydroxide. The resulting solution was extracted with 5×10 ml portions of ethyl acetate. The organic layers were combined, dried over sodium sulfate and evaporated n vacuo. The residue was chromatographed on silica gel eluting with ethyl acetate to afford 34 mg of the title compound as a colorless oil.

EXAMPLE 27

1-Piperazineacetic acid, [2S-[2α(E,E),3β,4α,5α,]]-tetrahydro-4-methoxy-5-methyl-2-(1-methyl-1,3,5-heptatrienyl)-2H-pyran-3-yl ester

A. 4-[(1,1-Dimethylethoxy)carbonyl]-1-piperazineacetic acid, phenylmethyl ester To a solution of N-BOC-piperazine (10.0 g, 53.7 mmol) and triethylamine (22.42 ml, 161 mmol) in ethyl acetate (100 ml) was added dropwise benzylbromo acetate (9.4 ml, 59.1 mmol) and the mixture stirred for one hour at room temperature. The precipitate was filtered off by suction and the filtrate washed with water and with brine. The organic layer was dried over sodium sulfate and evaporated n vacuo to provide 18.5 g of the title A product.

B. 4-[(1,1-Dimethylethoxy)carbonyl]-1-piperazineacetic acid

To a solution of the title A compound (16.5 g, 49.3 mmol) in methanol (200 ml) was added palladium on carbon (1.0 g) and the mixture hydrogenated for one hour. The catalyst was filtered off by suction and the filtrate evaproated n vacuo to provide 9.78 g of the title B product.

C. 1-Piperazineacetic acid, [2S-[2α(E,E),3β,4α,5α]]-tetrahydro-4-methoxy-5-methyl-2-(1-methyl-4-phenyl-1,3-butadienyl)-2H-pyran-3-yl ester To a solution of the title compound of Example 9 (0.3 g, 1.19 mmol) in methylenechloride (60 ml) was added ethyl-3-(3-dimethylamino) propyl carbodiimide hydrochloride (0.91 g, 4.76 mmol), the title B compound (1.16 g, 4.76 mmol), and a catalytic amount of dimethylaminopyridine. The mixture was stirred for two days at room temperature under argon, washed with water and evaporated n vacuo. The crude material was purified by chromatography on silica gel using ethyl acetate-petroleum ether (1:1) as eluent to provide 0.373 g of the title C compound.

D. 1-Piperazineacetic acid, [2S-[2α(E,E,E),3β,4α,5α,]]-tetrahydro-4-methoxy-5-methyl-2-(1-methyl1,3,5-heptatrienyl)-2H-pyran-3-yl ester The title C compound (0.34 g, 0.71 mmol) was dissolved in formic acid (6.0 ml) and stirred for 60 minutes at room temperature under argon. The pH was adjusted to 7.2 by the addition of aqueous ammonia and the mixture extracted with ethyl acetate. The organic layer was dried over sodium sulfate and evaporated vacuo. The crude product was purified by chromatography on silica gel using ethyl acetate with an increasing amount of methanol (20–50%) as eluent to provide 118 mg of the title compound.

EXAMPLE 28

[2α(E,E,E),3β,4α,5α]-Tetrahydro-3-(1H-imidazol-2-ylmethoxy)-4-methoxy-5-methyl-2-(1-methyl-1,3,5-heptatrienyl)-2H-pyran

A.
1-[[2-(Trimethylsilyl)ethoxy]methyl]-1H-imidazole-2-methanol

A solution of 1-[[2-(trimethylsilyl)ethoxy]methyl]-1H-imidazole-2-carboxaldehyde (prepared according to procedures described by J. P. Whitten et al., *J. Org. Chem.*, 51 (1986), 1891) (9.95 g, 44.0 mmol) in dry ether (40 ml) was dropped into a suspension of lithium aluminum hydride (0.42 g, 12.0 mmol) in dry ether (40 ml) and stirring was continued for 4 hours at room temperature. Then ice-water was added carefully, and the precipitated aluminum hydroxide was filtered off and washed with ether. The aqueous phase was separated and the organic phase was washed with water, dried over sodium sulfate an evaporated in vacuo to leave an oil (9.0 g) which crystallized spontaneously. Yield: 7.1 g, m.p. 68°–69° C. (from pentane).

B.
2-(Chloromethyl)-1-[2-(trimethylsilyl)ethoxy]methyl]-1H-imidazole, monohydrochloride Thionyl chloride (1.4 ml, 19.0 mmol) was added dropwise to a solution of the title A compound (3.7 g, 16.0 mmol) in dry dimethylformamide (90 ml) at 0° C. and stirring was continued at this temperature for 10 minutes and then, the mixture was allowed to warm up to room temperature. After 4 hours the solvent was removed in vacuo and the residue was solidified by stirring with dry ether. The solid was collected by suction, washed with few ml dry pentane and dried in vacuo. Yield: 3.35 g, m.p.=sint. 118°, 139° dec.

C.
[2α(E,E,E),3β,4α,5α]-Tetrahydro-4-methoxy-5-methyl-2-(1-methyl-1,3,5-heptatrienyl)-3[[1-[[2-(trimethylsilyl)ethoxy]methyl]-1H-imidazol-4-yl]methoxy-2H-pyran Under argon sodium hydride (60% dispersion in mineral oil) (110 mg, 2.8 mmol) was added slowly to a solution of the title compound of Example 9 (285 mg, 1.15 mmol) in dry dimethylsulfoxide (10 ml) and the mixture was stirred for 20 minutes at room temperature. Then the title B compound (360 mg, 1.27 mmol) was added in small portions within 25 minutes and stirring was continued at room temperature for 3 hours. After careful addition of ice-water and ether the pH of the mixture was lowered to 5 by addition of diluted citric acid and the mixture was extracted with ether. The organic layer was washed with brine, dried over sodium sulfate and evaporated in vacuo to leave an oil (0.46 g) which was chromatographed on silica gel eluting with ethyl acetate/pentane (3:2). The relevant fractions (#39–55) were stabilized with a trace BHT and then evaporated n vacuo to yield 320 mg of the desired title C compound as a viscous oil.

D.
[2α(E,E,E),3β,4α,5α]-Tetrahydro-3-(1H-imidazol-2-ylmethoxy)-4-methoxy-5-methyl-2-(1-methyl-1,3,5-heptatrienyl)-2H-pyran Under argon, the title C compound (0.51 mg, 1.1 mmol) was dissolved in dry tetrahydrofuran (30 ml) and dried with molecular sieves (4 Å, 1–2 mm beads) for 1 hour. After removal of the molecular sieves by filtration a 1.0M solution of tetrabutylammonium fluoride in tetrahydrofuran (5.0 ml, 5.0 mmol) was added, followed by molecular sieves (4 Å, powder). The mixture was stirred at 50° C. for 3 hours, cooled, filtered and evaporated in vacuo. The oily residue was taken up in ethyl acetate and ice-water, the organic layer was separated, washed with brine, stabilized with BHT, dried over sodium sulfate and evaporated in vacuo. The residual oil (0.35 g) was chromatographically purified on silica gel eluting with ethyl acetate/ethanol (95/5). Evaporation of the relevant fractions (#24–39) in vacuo afforded an oil which crystallized spontaneously to provide 144 mg of the title product (m.p.=152° C. sint; 164° dec.)

EXAMPLE 29

[2α(E,E,E),3β,4α,5α]-Tetrahydro-3-(1H-imidazol-4-ylmethoxy)-4-methoxy-5-methyl-2-(1-methyl-1,3,5-heptatrienyl)-2H-pyran

A. 4-(Chloromethyl)-1-(triphenylmethyl)-1H-imidazole hydrochloride

Thionyl choride (0.79 ml, 10.8 mmol) was added dropwise to dry dimethylformamide (70 ml) at 0° C. and stirring was continued at this temperature for 30 minutes. Then, under stirring and at 0° C. 4-(N-triphenylmethyl)imidazolyl methanol (prepared according to J. L. Kelley et al., *J. Med. Chem.*, 20 (1977), 721) (3.06 g, 9.0 mmol) was added slowly and the mixture was allowed to warm up to room temperature. After 3 hours the solvent was removed in vacuo and the residue was solidified by stirring with dry ether. The solid was collected by suction, washed with few ml dry ether and dried in vacuo. Yield: 2.9 g, m.p.=115°–118.5° C. The title A hydrochloride contained only a trace of dimethylformamide and was used in the next stage without any further purification.

B. 4-(Chloromethyl)-1-(triphenylmethyl)-1H-imidazole

Triethylamine (2.23 g, 22.0 mmol) was added slowly to a suspension of the title A compound (4.42 g, 11.0 mmol) in dry toluene (100 ml). After stirring for 15 minutes the precipitated triethylamine hydrochloride (2.5 g) was removed by suction and the filtrate was evaporated in vacuo. The residue was stirred with dry ether (150 ml) for 15 minutes, filtered and the filtrate was evaporated in vacuo to leave the pure title B compound. Yield: 3.16 g, m.p. 138° sint, 142°–144° C.

Elemental analysis calc'd for $C_{23}H_{19}ClN_2$ C, 76.98; H, 5.34; N, 7.81; Cl, 9.88;

Found: C, 77.07; H, 5.36; N, 7.54; Cl, 9.68.

C.
[2S-[2α(E,E,E),3β,4α,5α]]-Tetrahydro-4-methoxy-5-methyl-2-(1-methyl-4-phenyl-1,3-butadien-yl]-3-[1-(triphenylmethyl)-1H-imidazol-4-yl]methyl-2H-pyran Under argon sodium hydride (60% dispersion in mineral oil) (42 mg, 1.05 mmol) was washed with dry pentane to remove the mineral oil and then a solution of the title compound of Example 9 (240 mg, 0.95 mmol) in dry dimethylsulfoxide (7 ml) was added and the mixture was stirred for 15 minutes at room temperature. Then the title B compound (377 mg, 1.05 mmol) was added and stirring was continued at room temperature for 2 hours. After careful addition of ice-water and ether the pH of the mixture was lowered to 5 by addition of diluted citric acid and the mixture was extracted with ether. The organic layer was washed with brine, dried over sodium sulfate and evaporated in vacuo to leave an oil (0.71 g) which was chromatographed on silica gel eluting with pentane/ether (1:1). The relevant fractions (#221-319) were stabilized with a trace BHT and then evaporated n vacuo to yield 350 mg of the desired title C compound as a viscous oil.

D.
[2α(E,E,E),3β,4α,5α]-Tetrahydro-3-(1H-imidazol-2-ylmethoxy)-4-methoxy-5-methyl-2-(1-methyl-1,3,5-heptatrienyl)-2H-pyran The title C compound (480 mg, 0.84 mmol) was dissolved in a mixture of acetic acid (30 ml) and water (6 ml) and then treated at 45°-50° for 20 minutes. After removal of the solvent n vacuo, the residual oil was taken up in ethyl acetate and ice-water and the pH of the mixture was adjusted to 7.5 by addition of sodium hydrogen carbonate. The organic layer was separated, stabilized by addition of a trace BHT, evaporated in vacuo and chromatographically purified on silica gel eluting with ethyl acetate/ethanol (4:1). After separation of triphenylcarbinol (160 mg) and recovered starting material (70 mg), the relevant fractions were combined, stabilized by addition of a trace BHT and evaporated n vacuo to leave an oil (170 mg) which solidified by stirring with pentane to yield 120 mg of the title product (m.p. 61-62 dec).

EXAMPLE 30

Glycine,
[2S-[2α(E,E,E),3β,4α,5α]-Tetrahydro-4-methoxy-5-methyl-2-(1-methyl-6-phenyl-1,3,5-hexatrienyl)-2H-pYran-3-yl ester A.
[2S-[2α(E,E,E),3β,4α,5α]]-3-[[(1,1-Dimethylethyl)-dimethyldilyl]oxy]tetrahydro-4-methoxy-5-methyl-2-(1-methyl-6-phenyl-1,3,5-hexatrienyl-2H-pyran (E Isomer) and

[2S-[2α(E,Z,E),3β,4α,5α]-3-[(1,1-Dimethylethyl)dimethylsilyl]oxy]tetrahydro-4-methoxy-5-methyl-2-(1-methyl-6-phenyl-1,3,5-hexatrienyl)-2H-pyran (Z Isomer)

1.6M Solution of n-butyl lithium (0.26 ml, 0.42 mmol) in hexane was added dropwise to a sonicated suspension of 3-phenylallyltriphenylphosphonium bromide (175 mg, 0.38 mmol) in 10 ml dry toluene under argon. After 15 minutes a solution of the title compound of Example 21A (125 mg, 0.38 mmol) was added to the homogeneous reaction mixture and the mixture was stirred for 15 minutes with sonication. The mixture was washed three times with a pH 3.5 buffer solution, dried and evaporated. The crude product was chromatographed on silica gel with ether/petroleum ether 4:96 to give 108 mg of a mixture of the (E)- and (Z)-isomers. (The isomers were separated to a great extent when the chromatography was run with a 1:99 ratio). -

E-isomer ¹H NMR (CDCl₃)δ= −0.11, −0.02 (2s, 6H); 0.75 (s, 9H); 0.97 (d, 3H); 1.77 (d, 3H); 2.15 (m, 1H); 3.08 (dd, 1H); 3.25 (s, 3H); 3.40-3.60 (m, 3H); 3.72 (dd, 1H); 6.12 (d, 11.0 Hz, 1H); 6.33 (dd, 10.2+14.5 Hz, 1H); 6.52 (d, 15.5 Hz, 1H); 6.53 (dd, 11.0+14.5 Hz, 1H); 6.86 (dd, 10.2+15.5 Hz, 1H); 7.10-7.40 (m, 5H); ppm. Z-isomer: ¹H NMR (CDCl₃)δ= −0.06, 0.02 (2s, 6H); 0.77 (s, 9H); 1.02 (d, 3H); 1.77 (d, 3H); 2.20 (m, 1H); 3.12 (m 1H); 3.29 (s, 3H); 3.40-3.65 (m, 3H); 3.78 (dd, 1H); 6.05-6.30 (m, 2H); 6.40-6.70 (m, 2H); 7.15-7.45 (m, 6H); ppm.

B.
[2S-[2α(1E),3β,4α,5α]]-Tetrahydro-4-methoxy-5-methyl-2-(1-methyl-6-phenyl-1,3,5-hexatrienyl)-2H-pyran-3-ol To a solution of the title A isomers (270 mg, 0.63 mmol) in 15 ml dry tetrahydrofuran were added a few grams of mol sieve (4 A). After stirring for 0.5 hours 2.86 ml (3.15 mmol) tetrabutylammonium fluoride (1.1M solution in tetrahydrofuran) were added. After stirring for 1.5 hours, the solvent was distilled off, the residue taken up in ethyl acetate and filtered. The organic phase was washed with water and brine, dried and evaporated to give 392 mg of crude product which was used in the next step without further purification.

C. [[(1,1-Dimethylethoxy)carbonyl]amino]acetic acid, [2S-[2α(E,E,E),3β,4α,5α]-tetrahydro-4-methoxy-5-methyl-2-(1-methyl-6-phenyl-1,3,5-hexatrienyl)-2H-pyran-3-yl ester Under an argon atomsphere BOC-glycine (440 mg, 2.52 mmol), ethyl-3-(3-dimethylamino)propyl carbodiimide (480 mg, 2.52 mmol) and 17 mg dimethylamino pyridine were added to a solution of the title B compound (390 mg) in 20 ml dichloromethane. After stirring overnight at room temperature, the mixture was washed with water, dried and evaporated to give 587 mg of the crude product. The crude product was chromatographed on silica gel using ether/petroleum ether 1:4 as eluent. The product-containing fractions (136-250) were combined and evaporated to yield 118 mg of the (E,E,E)-isomer and in the forerun (fractions 85-135) 110 mg of a mixture of two isomers, containing mainly the (E,Z,E)-isomer.

(E,E,E)-isomer: ¹H NMR (CDCl₃)δ=1.08 (d, 3H); 1.38 (s, 9H); 1.80 (d, 3H); 2.25 (m, 1H); 3.32 (s, 3H); 3.39 (dd, 1H); 3.50-4.05 (m, 5H); 4.90 (s, broad, 1H); 5.03 (t, 1H); 6.03 (d, 10.5 Hz, 1H); 6.34 (dd, 9.8+14.7 Hz, 1H); 6.49 (dd, 10.5+14.7 Hz, 1H); 6.53 (d, 15.6 Hz, 1H); 6.82 (dd, 9.8+15.6 Hz, 1H); 7.10-7.40 (m, 5H); ppm.

D. Glycine,
[2S-[2α(E,E,E),3β,4α,5α]-Tetrahydro-4-methoxy-5-methyl-2-(1-methyl-6-phenyl-1,3,5-hexatrienyl)-2H-pyran-3-yl ester The title C compound (110 mg, 0.24 mmol) was dissolved in 5 ml formic acid and stirred for 1.5 hours at room temperature (tlc monitoring). The volatiles were distilled off in vacuo and the residue dissolved in ethyl acetate. The solution was washed twice with buffer solution pH 7, dried and evaporated to give 81 mg of the crude product. The crude product was chromatographed on silica gel using ethyl acetate/acetonitrile 9:1 as eluent. The product-containing fractions (18-40) were combined and evaporated to yield 60 mg of the title compound. The compound was again chromatographed on silica gel using the same conditions and afforded 37 mg of the title compound IR (film in CDCl₃) 1745 cm⁻¹ (CO) ¹H NMR (CDCl₃)δ=1.07 (d, 3H); 1.80 (d, 3H); ca. 2.20 (buried under water/NH₂, m, 1H); 3.28 (s. 3H) 3.33 (dd, 1H): 3.40-3.90 (m, 5H); 5.03 (t, 1H); 6.06 (d, 10.6 Hz, 1H): 6.36 (dd, 9.8+14.7 Hz, 1H): 6.51 (dd, 10.6+14.7 Hz, 1H); 6.54 (d, 15.5 Hz, 1H); 6.81 (dd, 9.8+15.5 Hz, 1H); 7.10-7.40 (m, 5H); ppm.

EXAMPLE 31

[2α(E,E,E),3β,4α,5α]-[[Tetrahydro-4-methoxy-5-methyl-2-(1-methyl-1,3,5-heptatrienyl)-2H-pyran-3-yl]oxy]acetic acid, ethyl ester Under argon a solution of the title compound of Example 9 (240 mg, 0.95 mmol) in dry benzene (5 ml) was added to a stirred solution of thallium(I) ethoxide (741 mg, 2.97 mmol) in dry benzene (15 ml) and stirring was continued at room temperature for 1 hour. The mixture was evaporated in vacuo and the residue was suspended in dry acetonitrile (15 ml). Then ethyl bromoacetate (496 mg, 2.97 mmol) was added dropwise and the mixture was stirred at room temperature for 18 hours. After addition of ether and ice-water the pH of the mixture was lowered to 5 by addition of buffer-solution (citrate), unsoluble material was filtered off and the organic layer was separated and the aqueous phase was extracted twice with ether. The combined organic layers were washed with few ml water, dried over sodium sulfate and evaporated in vacuo. The oily residue (510 mg) was chromatographed carefully on silica gel eluting with pentane/ether (3:2) to afford 120 mg of the desired title compound and 100 mg of the starting material.

EXAMPLE 32

[2α(E,E,E),3β,4α,5α]-[[Tetrahydro-4-methoxy-5-methyl-2-(1-methyl-1,3,5-heptatrienyl)-2H-pyran-3-yl]oxy]acetic acid, (1,1-dimethylethyl) ester Under argon sodium hydride (97 mg, 2.43 mmol) was washed with dry pentane to remove the mineral oil and then a solution of the title compound from Example 9 (558 mg, 2.21 mmol) in dry dimethylsulfoxide (9 ml) was added dropwise and the mixture was stirred for 15 minutes at room temperature. Then t-butyl bromoacetate (0.39 ml, 2.43 mmol) was added and stirring was continued at room temperature for one day. After careful addition of ice-water and ether the pH of the mixture was lowered to 5 by addition of diluted citric acid and the mixture was extracted with ether. The organic layer was washed with brine, dried over sodium sulfate and evaporated in vacuo to leave an oil (0.96 g) which was chromatographed on silica gel eluting with pentane-ethyl acetate. The relevant fractions were stabilized with a trace BHT and then evaporated in vacuo to yield the desired title compound (241 mg) which can be crystallized from pentane, m.p. 72.7°–73.7° C. Elemental analysis calc'd for $C_{21}H_{34}O_5$: C, 68.82; H, 9.35;
Found: C, 68.80; H, 9.37.

EXAMPLE 33

[2α(E,E,E),3β,4α,5α]-[[Tetrahydro-4-methoxy-5-methyl-2-(1-methyl-1,3,5-heptatrienyl)-2H-pyran-3-yl]oxy]ethanol Under argon a solution of the title compound of Example 32 (73 mg, 0.2 mmol) in dry ether (2.0 ml) was dropped into a suspension of lithium aluminum hydride (5 mg, 0.14 mmol) in dry ether (1.0 ml) and the mixture was stirred at room temperature for 3 hours. After addition of a trace of ethyl acetate and a trace of ethanol ice-water was added and the pH of the mixture was adjusted to 4–5 by addition of diluted sulfuric acid. The organic layer was separated and the aqueous phase was extracted twice with ether. The combined organic layers were dried over sodium sulfate, evaporated in vacuo and the residual oil was purified by chromatography on silica gel eluting with n-pentane/ethyl acetate (1:1) to provide 36 mg of the title compound as an oil.

EXAMPLE 34

Thioacetic acid, [2S-[2α(E,E,E),3β,4α,5α]-tetrahydro-4-methoxy-5-methyl-2-(1-methyl-1,3,5-heptatrienyl)-2H-pyran-3-yl ester A. Methyl 5,5-dimethyl-3,4-dithiahexanoate To a solution of 1-(tert-butylthio)-1,2-hydrazinedicarboxmorpholide (3.71 g, 10.71 mmol) in 70 ml dimethylformamide was added dropwise a solution of methyl mercaptoacetate (0.38 g, 3.57 mmol) in 50 ml dimethylformamide. After stirring overnight at room temperature the volatiles were distilled off in vacuo and the residue triturated with petroleum ether. The resulting solid was filtered off and the filtrate evaporated. The remaining oil was distilled to give 663 mg of the title A compound, b.p. 55°–60° C./0.1 mbar. IR (film): 1740 $cm^{-1}$, (ester) $^1H$ NMR $(CDCl_3)\delta = 1.35$ (s, 9H); 3.50 (s, 2H); 3.75 (s, 3H); ppm.

B. 5,5-Dimethyl-3,4-dithiahexanoic acid

To a solution of sodium hydroxide (0.37 g, 9.29 mmol) in 30 ml methanol/water 2:1 v/v, the title A compound (0.60 g, 3.10 mmol) was added and the mixture was stirred at room temperature for 2 hours. Methanol was removed in vacuo, and the pH was brought to 1 with diluted hydrochloric acid. The solution was extracted twice with ethyl acetate and the organic phase washed with water, dried and evaporated to give 532 mg of the title B compound IR (film): 1710 $cm^{-1}$, (CO). $^1H$ NMR $(CDCl_3)\delta = 1.37$ (s, 9H); 3.52 (s, 2H); 9.70 (s, braod, 1H); ppm.

C. [(1,1-Dimethylethyl)dithio]acetic acid, [2S-[2α(1E),3β,4α,5α]]-tetrahydro-4-methoxy-5-methyl-2-(1-methyl-6-phenyl-1,3,5-hexatrienyl)-2H-pyran-3-yl ester To a solution of the lanomycin alcohol title compound of Example 9 (0.20 g, 0.79 mmol) in 20 ml dichloromethane were added under argon, the title B compound (0.53 g, 2.95 mmol), ethyl-3-(3-dimethylamino)-propyl carbodiimide×HCl (0.61 g, 3.17 mmol) and 387 mg dimethylamino pyridine. The mixture was stirred for 3 hours at room temperature under inert gas atmosphere The solution was triturated with water, the phases separated and the water phase extracted twice with dichloromethane. The combined organic phases were dried and evaporated and the crude product chromatographed on 80 g silica gel with ethyl acetate/petroleum ether 1:4 as eluent. The sample containing fractions were collected and evaporated to give 362 mg of the title C compound as an oil. IR (film): 1740 $cm^{-1}$, (CO).
$^1H$ NMR $(CDCl_3)\delta = 1.07$ (d, 3H, 5—CHa); 1.52 (s, 9H), 'Bu); 1.73 (d, 3H, 13—H); 1.75 (s, 3H, 7—$CH_3$), 2.23 (m, 1H, 5—H), 3.31 (s, 3H, $OCH_3$), 15 3.38 (s, 2H, CO—$CH_2$—S), 3.36 (dd, 1H, 4—H), 3.45-3.6 (m, 2H, 2—H and 6—H), 3.80 (dd, 1H, 6—H), 5.00 (t, 1H, 3—H), 5.67 (m, 1H, 12—H), 5.90-6.30 (m, $4H_{tiene}$); ppm.

D. Thioacetic acid, [2S-[2α(E,E,E),3β,4α,5α]]-tetrahydro-4-methoxy-5-methyl-2-(1-methyl-1,3,5-heptatrienyl)-2H-pyran-3-yl ester To a solution of the title C compound (324 mg, 0.78 mmol) in 15 ml trifluoroethanol, 15 ml tert-butylmethyl ether and 0.3 ml water (the solvents were saturated with argon), tributylphosphine (221 mg, 1.09 mmol) was added and the mixture was stirred for 1 hour at room temperature under argon. The volatiles were distilled off in vacuo and the residue chromatographed on silica gel with ether/pentane 1:4 as eluent (ether and pentane were saturated with argon). The sample containing fractions were collected and evaporated to give 178 mg (fraction I) and 45 mg (fraction II) of the title compound as an oil. IR (film): 1740 cm$^{-1}$ (CO); 2560 cm$^{-1}$ (SH).

$^1$H NMR (CDCl$_3$)δ=1.07 (d, 3H, 5—CH$_3$); 1.72 (d, 3H, 13—H); 1.75 (s, 3H, 7—CH$_3$); 1.83 (t, 1H, SH); 2.23 (m, 1H, 5—H); 3.12 (d, 2H, CO—CH$_2$—S); 3.31 (s, 3H, OCH$_3$); 3.33 (dd, 1H, 4—H); 3.45-3.65 (m, 2H, 2—H and 6—H), 3.00 (dd, 1H, 6—H); 4.98 (t, 1H, 3—H), 5.68 (m, 1H, 12—H), 5.05-6.50 (m, 4H$_{triene}$): ppm.

EXAMPLE 35

(Methylthio)acetic acid, [2S-[2α(E,E,E),3β,4α,5α]-tetrahydro-4-methoxy-5-methyl-2-(1-methyl-1,3,5-heptatrienyl)-2H-pyran-3-yl ester To a solution of the lanomycin alcohol title compound of Example 9 (0.090 g, 0.356 mmol) in 10 ml dichloromethane were added under argon (methylthio)acetic acid (0.151 g, 1.426 mmol), ethyl-3-(3-dimethylamino)propyl carbodiimide×HCl (0.273 g, 1.426 mmol) and 10 mg dimethylamino pyridine. The mixture was stirred for 1 hour at room temperature (tlc monitoring indicated end of the reaction after 10 minutes) and then extracted three times with degassed water. After evaporation the residue was chromatographed on silica gel with ethyl acetate/hexane 15:85 as eluent. The sample containing fractions were collected and evaporated to give 128 mg of the title compound as an oil. IR (film): 1730 cm$^{-1}$, (ester).

$^1$H NMR (CDCl$_3$)δ=1.07 (d, 3H, 5—CH$_3$); 1.75 (d, 3H, 13—H), 1.77 (d, 3H, 7—CH$_3$), 2.06 (s 3H, S—CH$_3$); 2.25 (m, 1H, 5—H); 3.08 (s, 2H, CO—CH$_2$—S), 3.31 (s, 3H, OCH$_3$), 3.37 (dd, 1H, 4—H), 3.5-3.6 (m, 2H, 6—H), 3.80 (dd, 1H, 2—H), 5.02 (t, 1H, 3—H), 5.69 (m, 1H, 12—H), 5.90-6.30 (m, 4H$_{triene}$); ppm.

EXAMPLE 36

(Methylsulfinyl)acetic acid, 2S-2α(E,E,E),-3β,4α,5α]]-tetrahydro-4-methoxy-5-methyl-2-(1-methyl-1,3,5-heptatrienyl)-2H-pyran-3-yl ester A. (Methylsulfoxy)acetic acid To a solution of (methylthio)acetic acid (3.20 g, 30.0 mmol) in 20 ml acetone were added 2.91 g (30.0 mmol) hydrogen peroxide and the mixture was stirred for 4 days at room temperature. The volatiles were distilled off in vacuo and the residual oil (3.64 g) recrystallized from ethyl acetate. Yield of the title A compound 2.11 g, m.p. 77°-82° C.

B. (Methylsulfinyl)acetic acid, [2S-[2α(E,E,E),-3β,4α,5α]-tetrahydro-4-methoxy-5-methyl-2-(1-methyl-1,3,5-heptatrienyl)-2H-pyran-3-yl ester To a solution of the lanomycin alcohol title compound of Example 9 (0.090 g, 0.356 mmol) in 10 ml dichloromethane were added under argon, the title A compound (0.174 g, 1.427 mmol), ethyl-3-(3-dimethylamino)propyl carbodiimide×HCl (0.273 g, 1.426 mmol) and 10 mg dimethylamino pyridine. The mixture was stirred for 4 hours at room temperature and after addition of 30 ml dichloromethane extracted three times with degassed water. After evaporation the residue was chromatographed on silica gel with an ethyl acetate/hexane gradient (1:1 up to 3:1) as eluent. The sample containing fractions (ethyl acetate/hexane 3:1) were collected and evaporated to give 100 mg of the title compound as an oil. IR (film): 1730 cm$^{-1}$, (ester).

$^1$H NMR (CDCl$_3$)δ=1.06 (d, 3H, 5—CH$_3$); 1.75 (m, 6H, 13—H and 7—CH$_3$); 2.25 (m, 1H, 5—H); 2.62 (s, 3H, SO—CH$_3$), 3.30 (s, 3H, OCH$_3$), 3.40, 3.55, 3.80 (3 mc, 6H, 2—H, 4—H, 6—H and CH$_2$—SO). 5 00 (t 1H 3—H), 5.72 (m, 1H, 12—H), 5.85-6.30 (m, 4H$_{triene}$); ppm.

EXAMPLE 37

(Methylsulfonyl)acetic acid, [2S-2α(E,E,E),3β,4α,5α]-tetrahydro-4-methoxy-5-methyl-2-(1-methyl-1,3,5-heptatrienyl)-2H-pyran-3-yl ester A. (Methylsulfonyl)acetic acid To a solution of (methylthio)acetic acid (3.20 g, 30.0 mmol) in 15 ml acetic acid were added with cooling hydrogen peroxide (5.83 g, 60.0 mmol) and the mixture was stirred for five days at room temperature. The volatiles were distilled off in vacuo and the residue dried for 8 hours in vacuo. The resulting oil crystallized on seeding overnight. The crystals were triturated with ether, filtered off with suction, washed with ether and dried to give 2.51 g of the title A compound, m.p. 112°-113° C.

B. (Methylsulfonyl)acetic acid, [2S0[2α(E,E,E),3β,4α,5α]-tetrahydro-4-methoxy-5-methyl-2-(1-methyl-1,3,5-heptatrienyl)-2H-pyran-3-yl ester To a solution of the lanomycin alcohol product of Example 9 (0.270 g, 1.07 mmol) in a mixture of 3 ml chloroform and 30 ml acetonitrile were added under argon, the title A compound (0.591 g, 4.28 mmol), ethyl-3-(3-dimethylamino)propyl carbodiimide×HCl (0.819 g, 4.28 mmol) and 30 mg dimethylamino pyridine. The mixture was stirred for 4 days at room temperature and after addition of a trace of butyl hydroxy toluene evaporated in vacuo. The residue was chromatographed on silica gel with an ethyl acetate/hexane gradient (1:3 up to 1:1) as eluent. The sample containing fractions (ethyl acetate/hexane 1:3) were collected and evaporated to give 176 mg of the title compound as an oil which was chromatographed a second time with an ether/pentane gradient (2:8 up to 1:1). Yield: 128 mg of the title compound. IR (film): 1740 cm$^{-1}$, (ester).

$^1$H NMR (CDCl$_3$)δ=1.06 (d, 3H, 5—CH$_3$), 1.75 (m, 6H, 13—H and 7—CH$_3$), 2.25 (m, 1H, 5—H), 2.99 (s, 3H, SO$_2$—CH$_3$), 3.31 (s, 3H, OCH$_3$), 3.41 (dd, 1H, 2—H), 3.55 (mc, 2H, 6—H, 4—H), 3.80 (2 mc, 3H, 6—H and CH$_2$—SO$_2$), 5.03 (t, 1H, 3—H), 5.72 (mc, 1H, 12—H), 5.92-6.25 (m, 4 H$_{triene}$); ppm.

EXAMPLE 38

[2R-(2α,3β,4α,5α)]-3-[[(1,1-Dimethylethyl)dimethylsilyl]oxy]-2-[1-[[(1,1,-dimethylethyl)dimethylsilyl]oxy]ethenyl]tetrahydro-4-methoxy-5-methyl-2H-pyran A solution of n-butyl lithium (2.5M in hexane, 0.20 ml, 0.50 mmol) in dry tetrahydrofuran (15 ml) was treated dropwise with diisopropylamine (0.07 ml, 0.50 mmol) with stirring at 0° C. The mixture was held at 0° C. for 30 minutes, and then cooled to −78° C. with stirring. A solution of t-butyl-dimethylsilylchloride (377 mg, 2.5 mmol) in dry tetrahydrofuran (1.5 ml) was added dropwise, followed by a solution of the title compound of Example 21A (151 mg, 0.50 mmol) in dry tetrahydrofuran (3 ml) and stirring was continued at −78° C. for 30 minutes. The stirred mixture was allowed to come to ambient temperature (30 minutes), the solvent was removed on a rotary evaporator, and the residue was partionated between ether and ice-cold water. After lowering the pH of the mixture from pH=7 to pH=5 by addition of diluted HCl, the organic phase was separated, washed with brine, dried over sodium sulfate and evaporated in vacuo to leave an oil (202 mg) which was chromatographed on silica gel eluting with pentane containing a trace of ether. The appropriate fractions (8 ml) were combined and then evaporated in vacuo to yield the desired title compound as a colorless oil. Yield: 128 mg.

EXAMPLE 39

[2S-(2α,3β,4α,5α)]-3-[[(1,1-Dimethylethyl)dimethylsilyl]oxy]tetrahydro-4-methoxy-5-methyl-2H-pyran-2-methanol A. [2R-(2α,3β,4α,5α)]-3-[[(1,1-Dimethylethyl)dimethylsilyl]oxy]tetrahydro-4-methoxy-5-methyl-2H-pyran-2-carboxylic acid, (1,1-dimethylethyl)dimethylsilyl ester A solution of the title compound of Example 38 (120 mg, 0.29 mmol) in dry dichloromethane (0.6 ml) and dry methanol (1.2 ml) was treated with ozone at −78° C. until the solution remained blue. The excess of ozone was removed by argon and then dimethylsulfide (0.07 ml) was added. The mixture was allowed to come to ambient temperature and was then evaporated in vacuo to leave an oil which was pure enough to be used in the next step. Yield: 118 mg.

B. [2S-(2α,3β,4α,5α)]-3-[[(1,1-Dimethylethyl)dimethylsilyl]oxy]tetrahydro-4-methoxy-5-methyl-2H-pyran-2-methanol Into a suspension of lithium aluminum hydride (4.0 mg, ca 0.1 mmol) in dry ether (1.5 ml) a solution of the title A compound (110 mg, 0.26 mmol) in dry ether (1.0 ml) was added dropwise. After being stirred at ambient temperature for 3.5 hours, the mixture was treated carefully with ice-water. The formed inorganic solid was removed by suction and the organic layer was separated, dried over sodium sulfate and evaporated in vacuo to leave an oil which was purified by chromatography on silica gel eluting with an n-pentane-ether gradient. Evaporation of the appropriate fractions in vacuo yielded the desired title compound as a colorless oil, yield: 60 mg.

EXAMPLE 40

[2R-(2α,3β,4α,5α)]-3-[[(1,1-Dimethylethyl)dimethylsilyl]oxy]tetrahydro-4-methoxy-5-methyl-2H-pyran-2-carboxaldehyde Into a stirred solution of oxalylchloride (0.07 ml, 0.81 mmol) in dry dichloromethane (3 ml) was dropped a solution of dry dimethylsulfoxide (0.11 ml, 1.49 mmol) in dry dichloromethane at −60° C. and stirring was continued at this temperature (−60° C.) for 15 minutes. Then a solution of the title compound of Example 39 (180 mg, 0.62 mmol) in dry dichloromethane (1 ml) was added slowly. After being stirred for additional 15 minutes at −60° C. triethylamine (0.43 ml, 3.1 mmol) was added slowly, the mixture was stirred for 10 minutes at −60° C. and then allowed to come to ambient temperature and stirred for 40 minutes at this temperature. The solvent was removed on a rotary evaporator, and the residue was partitionated between ether and ice-water. The organic phase was separated, dried over sodium sulfate and evaporated in vacuo to leave an oil (157 mg) which was chromatographed on silica gel eluting with ethyl acetate/petroleum ether (1:4). The relevant fractions were combined and then evaporated in vacuo to yield the desired title aldehyde as a pale yellowish oil. Yield 108 mg.

Biological Activity of Scopularin Ia

The following methodology was used to determine the miniumum inhibitory concentration (hereinafter referred to as MIC) of scopularin.

The aerobic test organisms were grown in approximately 15–20ml of Antibiotic Assay Broth (Difco) by inoculating (in tubes) the broth with a loopful of the organism from a BHI (Difco) agar slant. The inoculated tubes were incubated at 37° C. for 18 to 24 hours. These cultures are assumed to contain $10^7$ colony forming units (CFU) per ml and the cultures were diluted 1:100 to give a final inoculum level of $10^5$ CFU; dilutions were made with Yeast Beef Broth (Difco).

Scopularin was dissolved in an appropriate diluent at a concentration of 1,000 μg/ml. Two-fold dilutions were made in Yeast Beef Broth (Difco), resulting in a range from 1000 g/ml to 0.5 μg/ml. 1.5 ml of each dilution was placed into individual petri dishes to which 13.5ml of K-10 agar was added. The composition of K-10 agar is:

| | |
|---|---|
| Beef extract | 1.5 g |
| Yeast extract | 3.0 g |
| Peptone | 6.0 g |
| Dextrose | 1.0 g |
| Agar | 15.0 g |
| Distilled Water to . | 1000 ml |

The final drug concentration in the agar ranged from 100 μg/ml to 0.05 μg/ml. Organism growth control plates containing agar only were prepared and inoculated before and after the test plates. The organisms were applied to the agar surface of each plate with a Denly Multipoint Inoculator (which delivers approximately 0.001 ml of each organism) resulting in a final inoculum of $10^4$ CFU on the agar surface.

The plates were incubated at 37° C. for 18 hours and the MICs determined. The MIC is the lowest concentration of compound inhibiting growth of the organism.

The results of the agar dilution assay are illustrated in the following tables:

TABLE 1

| Organism | SC No.* | MIC (μg/ml) Scopularin |
|---|---|---|
| Candida albicans | 5314 | 50 |
| Candida albicans | 9177 | 50 |
| Candida albicans | 11,422 | 50 |
| Candida albicans | 10,580 | 50 |
| Candida albicans | 10,102 | 100 |
| Candida albicans | 9721 | 50 |
| Candida albicans (Bacilysin[R])** | 12,734 | 100 |

TABLE 1-continued

| Organism | SC No.* | MIC (μg/ml) Scopularin |
|---|---|---|
| Candida albicans (Aculeacin^R) | 14,021 | 50 |
| Candida albicans | 10,584 | 25 |
| Candida albicans | 10,585 | 50 |
| Candida tropicalis | 8159 | 25 |
| Candida tropicalis (AmphoB^R) | 2963 | 6.3 |
| Candida tropicalis (AmphoB^R) | 9861 | 25 |
| Candida tropicalis | 10,597 | 25 |
| Candida krusei (AmphoB^R) | 2967 | 0.4 |
| Candida krusei | 2969 | 1.6 |
| Candida krusei | 2968 | 1.6 |
| Candida parakrusei | 2621 | 0.8 |
| Candida parakrusei | 2966 | 1.6 |
| Candida pseudotropicalis | 11,241 | 25 |
| Candida guilliermondii | 2210 | 12.5 |
| Candida guilliermondii | 2996 | 0.4 |
| Candida stellatoidea | 2211 | 25 |
| Candida glabrata | 11,267 | 25 |

*SC No. is the number of the microorganism in the collection of E. R. Squibb & Sons, Inc., Princeton, New Jersey.
**^R represents resistance to the antibiotic named.

TABLE 2

| Organism | SC No. | MIC (μg/ml) Scopularin |
|---|---|---|
| Trichophyton mentagrophytes | 2637 | 0.2 |
| Epidermophyton floccosum | 9185 | 0.2 |
| Trichophyton rubrum | 9199 | 0.4 |
| Microsporum canis | 9237 | 0.4 |
| Aspergillus fumigatus | 2100 | 50 |

In addition to M.I.C. determinations, the following methodology was used to determine the activity of the compounds of this invention against yeasts. Fresh F-4 broth cultures of the test organisms were made from frozen vials. The broth cultures were incubated at 30° C. for 18 to 24 hours at which time the average cell count was assumed to be $5 \times 10^7$ CFU per ml. They were then used to inoculate flasks containing 300 ml of F-4 agar that had been melted and cooled to 48° C. in a temperature-controlled water bath. The inoculum consisted of 1.7 ml to give an inoculum level of about $2.8 \times 10^5$ CFU per ml. 25 ml of the inoculated agar was then poured into 150×15 mm sterile Petri dishes and allowed to harden.

The composition of the F-4 broth is:

| Tryptone | 5 g |
|---|---|
| Malt extract | 3 g |
| Glucose | 10 g |
| Yeast extract | 3 g |
| Distilled water to | 1000 ml. |

The medium was sterilized at 121° C. for 15 minutes at 15 psi.

F-4 agar has the same composition as the broth but with the addition of 15 g agar per liter.

Cellulose discs, 6.35 mm diameter, from Schleicher & Schuell, Inc., Keene, N.H., were charged with 10 μl of a solution composed of 1 mg/ml of lanomycin or scopularin in methanol. The discs were then placed on the surface of the inoculated agar plates of the test yeast strains, and the plates incubated at 30° C. for 18 to 24 hours. At that time, the diameter of the zones of inhibition was measured.

The results for lanomycin and scopularin in the agar diffusion assay with yeasts are:

TABLE 3

| Organism | | Zone diameter (mm) Lanomycin/Scopularin | |
|---|---|---|---|
| Candida tropicalis | SC 8159 | 29 | 30 |
| Candida tropicalis | SC 2963 | 28 | 32 |
| Candida albicans | SC 4314 | 32 | 37 |
| Candida quillermondi | SC 2996 | 29 | 32 |
| Candida quillermondi | SC 2210 | 30 | 31 |
| Candida glabrata | SC 9342 | 33 | 36 |
| Candida krusei | SC 2969 | 12 | 20 |
| Candida parakrusei | SC 2621 | 27 | 31 |
| Candida parakrusei | SC 2966 | 12 | 20 |
| Cryptococcus neoformis | SC 5817 | 21 | 25 |
| Saccaromyces cerevisiae | SGY 195 | 25 | 23 |
| Saccaromyces cerevisiae | SGY 379 | 30 | 30 |

SC and SGY denote organisms from the general culture collection of the Bristol-Myers Squibb Company.

Inhibition of the Cytochrome P450 Enzyme, Lanosterol Demethylase

The inhibition of lanosterol demethylase was determined by two methods: the spectrophotometric carbon monoxide binding assay of Omura and Sato (J. Biol. Chem. 239:2370–2378, 1964) and by a radiolabeled metabolic assay.

Cells of Candida albicans, SGY677, were grown overnight without shaking at 30° C. in a medium consisting of yeast extract 1%, peptone 2%, glucose 2% and distilled water. Cells were harvested by centrifugation and resuspended in 0.65M mannitol to an optical density at 600 nm of 2.5. At this density 1 ml of cells was equal to 6.7 mg constant dry weight (105° C. for 18 hours).

Scopularin and its alcohol derivative of Example 4 were added to the enzyme and the inhibition of carbon monoxide binding determined over a range of inhibitor concentrations. The concentrations which give 50% inhibition of carbon monoxide binding were $3.6 \times 10^{-5}$M for scopularin and $1.4 \times 10^{-5}$M for the alcohol.

The ability of scopularin and its alcohol to inhibit the lanosterol demethylase of Candida albicans can also be visualized by a metabolic assay. Candida albicans, SC5314, was grown overnight at 30° with shaking in the same medium as that used above. Cells were harvested by centrifugation and resuspended in water to give an optical density of 0.3 at 660 nm. 750 μl of this cell suspension, 300 μl of a medium containing 0.35 g Difco yeast nitrogen base without amino acids, 1 g glucose and distilled water to 10 ml, 100 μl of test material and distilled water were combined to give a final volume of 1.425 ml. This was incubated for 15 minutes at 30° C. with shaking, then 3 μCi $^{14}$C-acetate was added and continued to incubate for 1 hour. Cells were harvested by centrifugation and extracted with 2×0.5 ml methanol; centrifuged, decanted supernate and repeated the extraction with 0.5 μl methanol-benzene (1:1). Centrifuged, decanted; combined supernates, dried and resuspended in 100 μl chloroform-methanol (1:1). The aliquots were spotted onto silica gel 60 (Merck) plates and developed chromatographically in a solvent containing dichloromethane-acetone (60:1). The plate was dried and exposed to XR-5 film (Kodak) for 2 days. The film was developed and examined for depletion of $^{14}C$-ergosterol with a corresponding increase in $^{14}C$-lanosterol by comparison with authentic standards. Both scopularin and the alcohol of Example 4 caused the accumulation of lanosterol, consistent with inhibition of lanosterol demethylase at concentrations of $6.7 \times 10^{-7}$ and $1.4 \times 10^{-6}$, respectively.

Biological Activity of Lanomycin Ib

Lanoymcin was not active against Gram positive or Gram negative bacteria but showed activity against some Candida species and dermatophytes (Table 4). In a fuller examination of anticandidal activity (Table 5), it is found to be active against the *C. albicans* species tested, and showed good activity against certain strains of *C. krusei, C. parakrusei, C. guillermondii,* and *C. glabrata* (Table 5). Lanomycin was active against dermatophytes but inactive against *Aspergillus fumigatus* (Table 6). When lanomycin was administered intraperitoneally to random bred Swiss Webster Female mice in LD50 of 385 mg/kg was calculated.

TABLE 4

Antibacterial and antifungal activity of lanomycin

| Organism | SC No. | MIC (ug/ml)* |
|---|---|---|
| Staphylococcus aureus | 1276 | >100 |
| Staphylococcus aureus | 2399 | >100 |
| Micrococcus luteus | 2495 | >100 |
| Enterococcus faecalis | 9011 | >100 |
| Escherichia coli | 8294 | >100 |
| Klebsiella aerogenes | 10440 | >100 |
| Proteus mirabilis | 3855 | >100 |
| Pseudomonas aeruginosa | 8329 | >100 |
| Candida albicans | 5314 | >100 |
| Candida albicans | 11422 | 100 |
| Candida tropicalis | 2963 | 25 |
| Candida guillermondii | 2996 | 1.6 |
| Trichophyton mentagrophytes | 2637 | 0.8 |
| Trichophyton rubrum | 9199 | 1.6 |
| Epidermophyton floccosum | 9185 | 100/1.6** |
| Microsporum canis | 9237 | 100/1.6** |
| Aspergillus fumigatus | 2100 | 100 |

*Minimal inhibitory concentrations were determined by agar dilution assay.
**Higher value is based on hazy growth; lower value for clearly discernible growth.

TABLE 5

Anticandidal activity of lanomycin

| Organism | SC No. | MIC (ug/ml) |
|---|---|---|
| Candida albicans | 5314 | >100 |
| | 9177 | 100 |
| | 11422 | 100 |
| | 10580 | >100 |
| | 10102 | >100 |
| | 9721 | 100 |
| | 12734 | >100 |
| | 14021 | >100 |
| | 10584 | 50 |
| | 10585 | 100 |
| Candida tropicalis | 8159 | >100 |
| | 2963 | 25 |
| | 9861 | 100 |
| | 10597 | 100 |
| Candida krusei | 2967 | 6.3 |
| | 2968 | 12.5 |
| | 2969 | 25 |
| Candida parakrusei | 2621 | 12.5 |
| | 2966 | 25 |

TABLE 5-continued

Anticandidal activity of lanomycin

| Organism | SC No. | MIC (ug/ml) |
|---|---|---|
| Candida pseudotropicalis | 11241 | 50 |
| Candida guillermondii | 2210 | 50 |
| | 2996 | 1.6 |
| Candida stellatoidea | 2211 | 50 |
| Candida glabrata | 9342 | 0.8 |
| | 11267 | 25 |

MICs were determined by the agar dilution method using a medium composed of tryptone (5 g), malt extract (3 g), glucose (10 g) and yeast extract (3 g) in 1 L distiled water; $10^4$ cfu of the test organism was applied to the agar.

TABLE 6

Activity of lanomycin against filamentous fungi

| Organism | SC No. | MIC (ug/ml)* |
|---|---|---|
| Trichophyton mentagrophytes | 2637 | 0.4 |
| Trichophyton rubrum | 9199 | 1.6 |
| Epidermophyton floccosum | 9185 | 0.4 |
| Microsporum canis | 9237 | 0.4 |
| Aspergillus fumigatus | 2100 | 100 |

MICs were determined as in Table 5 except that the inoculum was $10^3$ cfu.

What is claimed is:

1. A compound of the formula

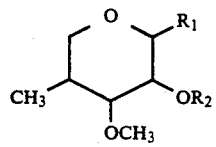

I wherein
R₁ is arylalkenyl;
R₂ is

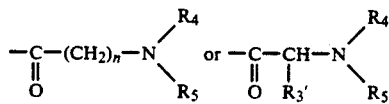

R₃ is hydrogen or alkyl; R₄ and R₅ are independently hydrogen or alkyl; and
n=1 to 3.

2. A compound of claim 1 having the name glycine, [2S-[2α(E,E),3β,4α,5α]]-tetrahydro-4-methoxy-5-methyl-2-(1-methyl-4-phenyl-1-butadienyl)-2H-pyran-3-yl ester.

3. A compound of claim 1 having the name glycine, [2S-[2α(E,Z),3β,4α,5α]]-tetrahydro-4-methoxy-5-methyl-2(1-methyl-4-phenyl-1-butadienyl)-2H-pyran-3-yl ester.

4. A compound of claim 1 having the name glycine, [2S-[2α(E,E,E),3β,4α,5α]]-tetrahydro-4-methoxy-5-methyl-2-(1-methyl-6-phenyl-1,3,5-hexatrienyl)-2H-pyran-3-yl ester.

5. A method of treating a fungal infection in a plant specie comprising administering to a specie in need thereof a therapeutically effective amount of a compound of claim 1.

6. A method of treating a fungal infection in a mammalian specie comprising administering to a specie in need thereof a therapeutically effective amount of a compound of claim 1.

* * * * *